United States Patent
Murray et al.

(10) Patent No.: US 9,694,047 B2
(45) Date of Patent: *Jul. 4, 2017

(54) ENHANCEMENT OF BONE MORPHOGENIC PROTEIN (BMP) RETENTION WITH BMP BINDING PEPTIDE (BBP)

(71) Applicant: REGENTS OF THE UNIVERSITY OF CALIFORNIA, Oakland, CA (US)

(72) Inventors: Samuel S. Murray, Saugus, CA (US); Elsa J. Murray, Saugus, CA (US); Jeffrey Wang, Sherman Oaks, CA (US); Keyvan Behnam, Simi Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/755,408

(22) Filed: Jun. 30, 2015

(65) Prior Publication Data
US 2016/0000860 A1    Jan. 7, 2016

Related U.S. Application Data

(63) Continuation of application No. 13/379,436, filed as application No. PCT/US2010/001819 on Jun. 23, 2010, now Pat. No. 9,072,709.

(60) Provisional application No. 61/269,433, filed on Jun. 23, 2009.

(51) Int. Cl.
| | |
|---|---|
| *A61K 38/10* | (2006.01) |
| *A61K 38/18* | (2006.01) |
| *A61K 35/32* | (2015.01) |
| *C07K 7/08* | (2006.01) |
| *C07K 14/51* | (2006.01) |
| *C07K 14/495* | (2006.01) |
| *A61K 38/12* | (2006.01) |
| *A61K 38/08* | (2006.01) |

(52) U.S. Cl.
CPC .............. *A61K 38/12* (2013.01); *A61K 38/08* (2013.01); *A61K 38/10* (2013.01); *A61K 38/1841* (2013.01); *A61K 38/1875* (2013.01)

(58) Field of Classification Search
None
See application file for complete search history.

(56) References Cited

U.S. PATENT DOCUMENTS

| | | | |
|---|---|---|---|
| 4,789,732 A | 12/1988 | Urist | |
| 4,843,063 A | 6/1989 | Seyedin et al. | |
| 5,158,934 A | 10/1992 | Ammann et al. | |
| 5,194,596 A * | 3/1993 | Tischer | C07K 14/46 530/350 |
| 5,350,836 A * | 9/1994 | Kopchick | A01K 67/0275 435/69.4 |
| 5,393,739 A | 2/1995 | Bentz et al. | |
| 5,407,810 A | 4/1995 | Builder et al. | |
| 5,620,867 A | 4/1997 | Kiefer et al. | |
| 5,981,483 A | 11/1999 | Dennis et al. | |
| 6,200,606 B1 | 3/2001 | Peterson et al. | |
| 6,291,428 B1 | 9/2001 | Macauley et al. | |
| 6,311,690 B1 | 11/2001 | Jefferies | |
| 6,322,786 B1 | 11/2001 | Anderson | |
| 7,241,874 B2 | 7/2007 | Thorne | |
| 8,188,219 B2 | 5/2012 | Murray et al. | |
| 8,193,312 B2 | 6/2012 | Murray et al. | |
| 8,415,302 B2 * | 4/2013 | Murray | A61K 38/1841 424/426 |
| 8,759,296 B2 * | 6/2014 | Murray | A61K 38/1841 424/426 |
| 8,975,231 B2 * | 3/2015 | Murray | A61K 38/1841 424/426 |
| 9,050,300 B2 * | 6/2015 | Murray | A61K 38/1841 |
| 9,333,237 B2 * | 5/2016 | Murray | A61K 38/1841 |
| 2003/0095993 A1 | 5/2003 | Bentz et al. | |
| 2006/0270645 A1 | 11/2006 | Parhami | |
| 2007/0056050 A1 | 3/2007 | Clokie et al. | |
| 2007/0065415 A1 | 3/2007 | Kleinsek et al. | |
| 2008/0234219 A1 | 9/2008 | Brunkow et al. | |

(Continued)

FOREIGN PATENT DOCUMENTS

| | | |
|---|---|---|
| EP | 0409472 | 1/1991 |
| JP | 4235197 | 8/1992 |

(Continued)

OTHER PUBLICATIONS

Ngo et al., 1994, The Protein Folding Problem and Tertiary Structure Prediction, Merz et al., eds., Birkhauser, Boston, pp. 492-495.*
Tokuriki et al., 2009, Curr. Opin. Struc. Biol. 19:596-604.*
Benjamin et al., 1998, Development 125:1591-1598.*
Vukicevic et al., 1996, PNAS USA 93:9021-9026.*
Shen et al., 2004, Eur. J. Neurosci. 20:2031-2037.*
Massague, 1987, Cell 49:437-8.*
Pilbeam et al., 1993, Bone 14:717-720.*
Supplementary European Search Report for EP05857032 dated Aug. 7, 2009.
International Search Report and Written Opinion for PCT/US2005/002722 dated Dec. 19, 2005.
International Search Report and Written Opinion for PCT/US2005/043215 dated Aug. 3, 2006.

(Continued)

*Primary Examiner* — Elizabeth C Kemmerer
(74) *Attorney, Agent, or Firm* — McDermott, Will & Emery LLP

(57) ABSTRACT

The use of autogenous bone graft is the current gold standard in the 1.5 million bone-grafting surgeries performed annually in the United States. Although this practice has resulted in high rates of fusion success, it is associated with increased operative time and blood loss, along with a significant degree of donor-site morbidity. Additionally, in certain settings such as revision cases, multilevel constructs, or in patients with medical co-morbidities, autogenous bone graft may exist in limited quantity and quality. This significant need for a suitable alternative to autogenous bone graft has stimulated great interest in the exploration of bone graft substitutes and extenders.

14 Claims, 13 Drawing Sheets

(56) References Cited

U.S. PATENT DOCUMENTS

| | | | |
|---|---|---|---|
| 2008/0241108 | A1 | 10/2008 | Murray et al. |
| 2008/0268012 | A1 | 10/2008 | Behnam et al. |
| 2009/0047360 | A1 | 2/2009 | Murray et al. |
| 2013/0095075 | A1 | 4/2013 | Murray et al. |
| 2013/0303449 | A1 | 11/2013 | Murray et al. |

FOREIGN PATENT DOCUMENTS

| | | |
|---|---|---|
| JP | 5085939 | 4/1993 |
| JP | H09505305 | 5/1997 |
| WO | WO9621006 | 7/1996 |
| WO | WO9731661 | 9/1997 |
| WO | WO9740137 | 10/1997 |
| WO | WO2004004630 | 1/2004 |
| WO | WO2004013294 | 2/2004 |
| WO | WO2004097424 | 11/2004 |
| WO | WO 2005/072403 A2 * | 8/2005 |
| WO | WO2005072403 | 8/2005 |
| WO | WO2006093545 | 9/2006 |
| WO | WO2008079400 | 8/2008 |
| WO | WO2009067177 | 5/2009 |

OTHER PUBLICATIONS

International Search Report and Written Opinion for PCT/US2007/026315 dated Jun. 17, 2008.
International Search Report and Written Opinion for PCT/US2008/012833 dated May 4, 2009.
Search Report for European Patent Application No. 05857032 dated Jul. 21, 2009.
Search Report for European Patent Application No. 07868028 dated Jul. 6, 2011.
Search Report for European Patent Application No. 08852773 dated Jul. 6, 2011.
Search Report for European Patent Application No. 10797441 dated Jun. 21, 2013.
Behnam, et al. "Alkali-urea Extraction of Demineralized Bone Matrix Removes Noggin, an Inhibitor of Bone Morphogenetic Proteins." Connective Tissue Research 2004, vol. 45, No. 4-5, pp. 257-260 (Jul. 2004).
Behnam, et al. "BMP Binding Peptide: a BMP-2 Enhancing Factor Deduced from the Sequence of Native Bovine Bone Morphogenetic Protein/Non-Collagenous Protein." Journal of Orthopaedic Research, vol. 23, pp. 175-180 (2005).
Behnam, et al. "Identification of the Molecular Chaperon Alpha B-Crystallin in Demineralized Bone Powder and Osteoblast-Like Cells." Journal of Orthopaedic Research, vol. 20(6), pp. 1190-1196 (Nov. 2002).
Bender, et al. "Sickle Cell Disease." NCBI Bookshelf. A service of the National Library of Medicine, National Institutes of Health, 1993-2013, Bookshelf ID: NBK1377PMID: 20301551.
Bennett, et al. "Characterization of the Human Secreted Phosphoprotein 24 Gene (SPP2) and Comparison of the Protein Sequence in Nine Species." Matrix Biology, vol. 22, No. 8, pp. 641-651 (2004).
Bowie, et al. "Deciphering the Message in Protein Sequences: Tolerance to Amino Acid Substitutions." Science, vol. 247, Mar. 16, 1990, pp. 1306-1310.
Brown, et al. "Friends and Relations of the Cystatin Superfamily—New Members and Their Evolution." Protein Science, vol. 6, pp. 5-12 (1997).
Carano, et al. "Angiogenesis and Bone Repair." Drug Discovery Today, vol. 8(21), pp. 980-989 (Nov. 2003).
Cook, et al. "In Vivo Evaluation of Recombinant Human Osteogenic Protein (rhOP-1) Implants as a Bone Graft Substitute for Spinal Fusions." Spine, vol. 19, No. 15, pp. 1655-1663 (1994).
Cook, et al. "Recombinant Human Bone Morphogenic Protein-7 Induces Healing in a Canine Long-Bone Segmental Defect Model". Clinical Orthopedics and Related Research, No. 301, pp. 302-312 (1994).
Chen, et al. "Bone Morphogenetic Proteins" Growth Factors, vol. 22, No. 4, pp. 233-241 (Dec. 2004).
Demetriou, et al. "Fetuin/α2-HS Glycoprotein is a Transforming Growth Factor-β Type II Receptor Mimic and Cytokin Antagonist." Journal of Biological Chemistry, vol. 271(22), pp. 12755-12761 (May 1996).
Dijke, et al. "Controlling Cell Fate by Bone Morphogenetic Protein Receptors." Molecular and Cellular Endocrinology, vol. 211, pp. 105-113 (2003).
Guo, et al. "Protein Tolerance to Random Amino Acid Change." Proc. Natl. Acad. Sci. U.S.A. Jun. 22, 2004; 101(25):9205-10.
Herrera-Esparza, et al. "An Activin Receptor IA/Activin-Like Kinase-2 (R206H) Mutation in Fibrodysplasia Ossificans Progressiva." Hindawi Publishing Corporation Case Reports in Genetics, vol. 2013, Article ID 260371 (2013).
Hu, et al. "Isolation and Molecular Cloning of a Novel Bone Phosphoprotein Related in Sequence to the Cystatin Family of Thiol Protease Inhibitors." Journal of Biological Chemistry, vol. 270(1), pp. 431-436 (Jan. 1995).
Madian, et al. "Effect of Single Amino Acid Substitution on Oxidative Modifications of the Parkinson's Disease-Related Protein, DJ-1." Molecular & Cellular Proteomics 11.2 (2012).
Mamidi, et al. "Alanine or aspartic acid substitutions at serine23/24 of cardiac troponin I decrease thin filament activation, with no effect on crossbridge detachment kinetics." Arch Biochem Biophys., vol. 525 (2012).
Miller-Bertoglio, et al. "Maternal and Zygotic Activity of the Zebrafish ogon Locus Antagonizes BMP Signaling." Developmental Biology, vol. 21, pp. 72-89 (1999).
Murray, et al. "Strain-Dependent Differences in Vertebral Bone Mass, Serum Osteocalcin, and Calcitonin in Calcium-Replete and -Deficient Mice." Pro. Soc. Exp. Biol. Med., vol. 203, pp. 64-73 (1993).
Murray, et al. "Recombinant Expression, Isolation, and Proteolysis of Extracellular Matrix-Secreted Phosphoprotein-24 kDa." Connect Tissue Res. 2007; 48(6):292-9.
Ngo, et al. "Computational Complexity, Protein Structure Prediction, and the Levinthal Paradox." The Protein Folding Problem and Tertiary Structure Prediction, Aug. 1994, Springer Verlag, pp. 433 and 492-495.
Notredame, et al., "T-Coffee: A Novel Method for Fast and Accurate Multiple Sequence Alignment." Journal of Molecular Biology, vol. 302, pp. 205-217 (2000).
Parfitt, et al. "Bone Histomorphometry: Standardization of Nomenclature, Symbols, and Units." Journal of Bone and Mineral Research, vol. 2(6) pp. 595-610 (1987).
Perron, et al. "Structural distinctions in BMPs underlie divergent signaling in spinal neurons." Neural Development, 7:16 (2012).
Ripamonti, et al. "Xenogeneic Osteogenin A Bone Morphogenetic Protein and Demineralized Bone Matrices Including Human Induce Bone Differentiation in Athymic Rats and Baboons." Matrix: Collagen and Related Research, vol. 11, No. 6, pp. 404-411 (Jan. 1991).
Sampath, et al. "Dissociative Extraction and Reconstitution of Extracellular Matrix Components involved in Local Bone Differentiation." Proceedings of the National Academy of Sciences of USA, vol. 78, No. 12, pp. 7599-7603 (Dec. 1981).
Sintuu, et al. Full-Length Bovine spp24 [spp24 (24-203)] Inhibits BMP-2 Induced Bone Formation. Journal of Orthopaedic Research, Jun. 2008, pp. 753-758.
Sintuu, et al. "Full-Length spp24, but Not Its 18.5-kDa Proteolytic Fragment, Inhibits Bone-Healing in a Rodent Model of Spine Fusion." Journal of Bone and Joint Surgery, vol. 93-A, No. 11, pp. 1022-1032 (2011).
Takahashi. "Bone Morphogenetic Protein (BMP): From Basic Studies to Clinical Approaches." Folia Pharmacologica Japonica, vol. 116, No. 4, pp. 232-240 (Oct. 2000).
Urist, et al. "Hydroxyapatite Affinity, Electroelution, and Radioimmunoassay for Identification of Human and Bovine Bone Morphogenetic Proteins and Polypeptides." Development and Diseases of Cartilage and Bone Matrix, pp. 149-176 (1987).
Urist, et al. "Preparation and Bioassay of Bone Morphogenic Protein and Polypeptide Fragments." Methods in Enzymology, vol. 146, pp. 294-312 (1987).

(56) References Cited

OTHER PUBLICATIONS

Urist, et al. "Purification of Bovine Bone Morphogenetic Protein by Hydroxyapatite Chromatography." Proc. Natl. Acad. Sci. USA, vol. 81, pp. 371-375 (Jan. 1984).

Urist. "Bone: Formation by Autoinduction." Science, vol. 150, pp. 893-899 (Nov. 1965).

Urist. "Emerging Concepts of Bone Morphogenetic Protein." Fundamentals of Bone Growth: Methodology and Applications, pp. 189-198 (1991).

Zhao, et al. "Targeted Overexpression of Insulin-Like Growth Factor I to Osteoblasts of Transgenic Mice: Increased Trabecular Bone Volume Without Increased Osteoblast Proliferation." Endocrinology, vol. 141(7), pp. 2674-2682 (2000).

\* cited by examiner

FIG. 1A

SEQ ID No 1:   Cys-Arg-Ser-Thr-Val-Arg-Met-Ser-Ala-Glu-Gln-Val-Gln-Asn-Val-Trp-Val-Arg-Cys
SEQ ID No 2:   TGC-AGA-AGC-ACC-GTG-CGG-ATG-TCT-GCT-GAA-CAG-GTG-CAG-AAC-GTG-TGG-GTT-CGC-TGC
               107                                                                        126

FIG. 1B cystatin homology region
              leader sequence    BMP-2 homology region
(1)   MAMKMLVIFVLGMNHWTCTGFPVYDYDPASLKEALSASVAKVNSQSLSPYLFRAFRSSVKRVNALDEDSLTMDLE (75)

cystatin homology region         TGF-β receptor II homology region
(76)  FRIQETTCRRESEADPATCDFQRGYHVPVAVCRSTVRMSAEQVQNVWVRCHWSSSSGSSSEEMFFGDILGSSTS (150)

(151) RNSYLLGLTPDRSRGEPLYEPSREMRRNFPLGNRRYSNPWPRARVNPGFE (200)   SEQ ID No 5

FIG. 2

| human BMP-2 | F | P | L | A | D | H | L | N | S | T | N | H | A | I | V | Q | T | L | V | N | S | K | SEQ ID NO 6 |
|---|---|---|---|---|---|---|---|---|---|---|---|---|---|---|---|---|---|---|---|---|---|---|---|
| human BMP-2 | F | P | V | Y | D | Y | D | P | A | S | L | K | E | A | L | S | A | S | V | K | S | Q | SEQ ID NO 7 |
|  | - | - | c | - | - | c | c | c | c | c | c | c | - | c | sc | sc | c | sc | sc | - | sc | sc |  |

FIG. 3

| bovine fetuin | 114 | C | D | I | H | V | L | K | Q | D | G | Q | F | S | V | L | F | T | K | C |  | SEQ ID NO 8 |
|---|---|---|---|---|---|---|---|---|---|---|---|---|---|---|---|---|---|---|---|---|---|---|
| human TGF-β receptor II | 84 | C | * | V | A | V | W | R | K | N | D | E | N | I | T | L | E | T | V | C |  | SEQ ID NO 8 |
|  |  | - | c | c | - | c | c | c | c | c | sc | c | c | sc | - | c | - | - | c | - |  |  |
| human TGF-β receptor II | 84 | C | V | A | V | W | R | K | N | D | * | * | * | E | I | T | L | E | T | V | C | SEQ ID NO 9 |
| bovine BBP |  | C | R | S | T | V | R | M | S | A | E | Q | V | N | W | V | R | * | * | C |  | SEQ ID NO 10 |
|  |  | - | c | sc | c | - | c | sc | sc | c | sc | sc | c | c | c | c | sc | * | * | - |  |  |

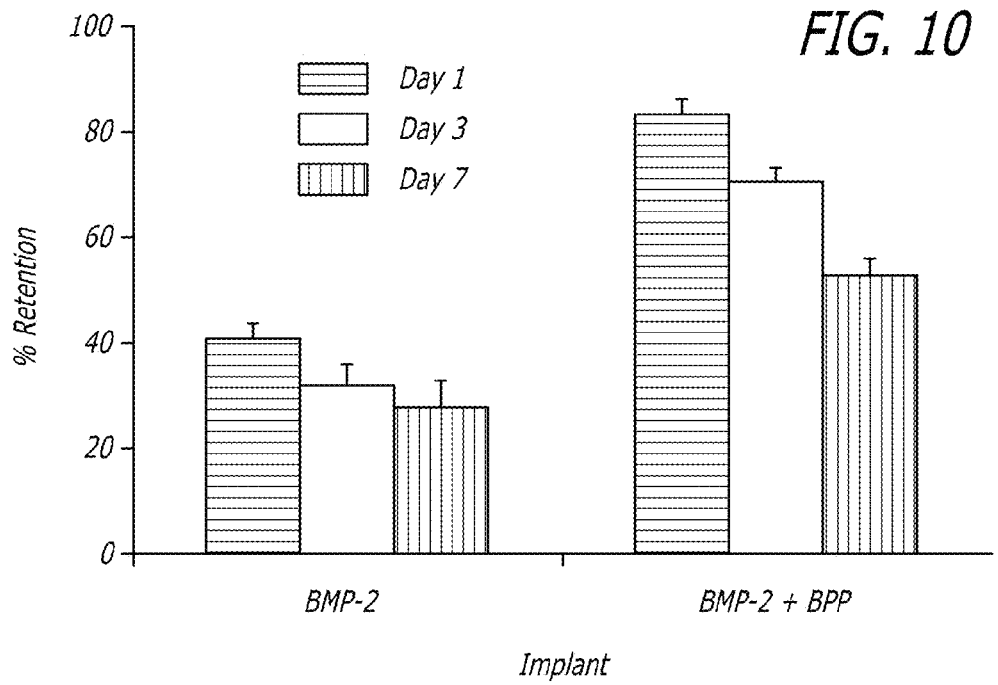
FIG. 10
FIG. 11
IQETTCRRESEADPATCDFQRGYHVPVAVCRSTVRMSAEQV (SEQ ID No 3)
CGEPLYEPSREMRRN" (SEQ ID NO 4 (SEQ ID No 4)
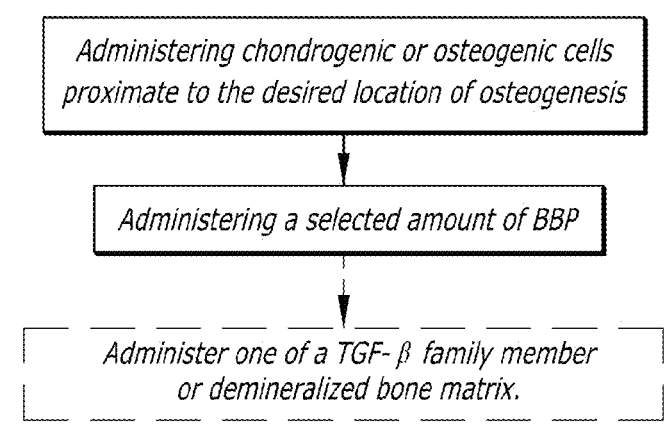
FIG. 12A

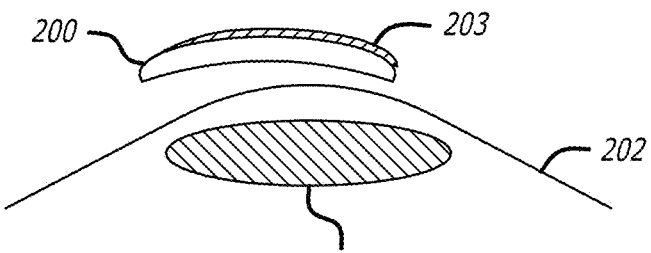
FIG. 12B
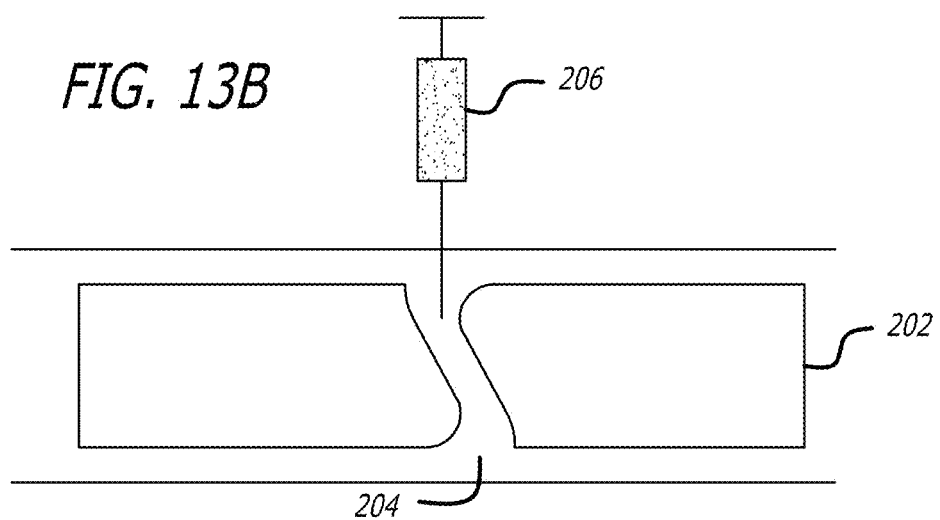
FIG. 13A
FIG. 13B

FIG. 14A

| Species | Position/Amino acid | 1 | 2 | 3 | 4 | 5 | 6 | 7 | 8 | 9 | 10 | 11 | 12 | 13 | 14 | 15 | 16 | 17 | 18 | 19 | SEQ. ID No. |
|---|---|---|---|---|---|---|---|---|---|---|---|---|---|---|---|---|---|---|---|---|---|
| Consensus | | C | R | S | T | V | X | Y | S | X | X | X | V | X | X | V | X | X | X | C | 11a |
| Bovine | | C | R | S | T | V | R | M | S | A | E | Q | V | Q | N | V | W | V | R | C | 1a |
| Human | | C | R | S | T | V | K | V | S | A/V* | Q | Q | V | Q | G | V | H | A | R | C | 12a |
| Porcine | | C | R | S | T | V | Q | I | S | A | E | K | V | Q | D | V | W | V | R | C | 13a |
| Ovine | | C | R | S | T | V | R | M | S | A | E | R | V | Q | D | V | W | V | R | C | 14a |
| Rat | | C | R | S | T | V | Q | M | S | K | G | Q | V | K | D | V | W | A | H | C | 15a |
| Mouse | | C | R | S | T | V | Q | M | S | K | G | Q | V | K | D | V | W | A | H | C | 16a |
| Chicken | | C | K | S | V | V | E | V | S | S | E | Q | I | V | N | V | I | V | R | C | 17a |
| Salmon | | C | T | A | R | V | R | V | T | A | E | F | T | Q | V | V | S | L | N | C | 18a |
| Trout | | C | T | A | R | V | R | V | T | A | E | L | T | Q | V | V | S | L | N | C | 19a |

* The amino acid at position 9 can be either A or V.

FIG. 14B

SEQ ID No. 11b: TGC AGA AGC ACC GTG XXX YYY TCT XXX XXX XXX GTG XXX TTT TTT TGC

SEQ ID No. 12b: TGC AGA AGC ACC GTG AAG GTA TCT GCC CAG CAG GTG CAT GCT CGC TGC

SEQ ID No. 13b: TGC AGA AGC ACC GTG CAG ATA TCT GCT GAG AAG GTG CAG GAT GTG TGG GTG CGT TGT

SEQ ID No. 14b: TGC AGA AGC ACC GTG CGG ATG TCT GCT GAA CGC GTG CAG GAC GTG TGG GTT CGC TGC

SEQ ID No. 15b: TGC AGG AGC ACA GTG CAG ATG TCC AAG GGA CAG GTG AAG GAT GTG TGG GCT CAC TGC

SEQ ID No. 16b: TGC AGG AGC ACT GTG CAG ATG TCC AAG GGA CAG GTA AAG GAT GTG TGG GCT CAC TGC

SEQ ID No. 17b: TGC AAA AGC GTT GTA GAA GTC TCC AGT GAG CAG ATT GTG AAT GTT ATT GTG CGA TGC

SEQ ID No. 18b: TGC ACC GCA CGT GTT CGC GTC ACT GCA GAG TTC ACT CAG GTT GTG TCC CTG AAC TGT

SEQ ID No. 19b: TGC ACC GCA CGT GTT CGT GTC ACT GCA GAG CTC ACT CAG GTT GTG TCC CTG AAC TGT

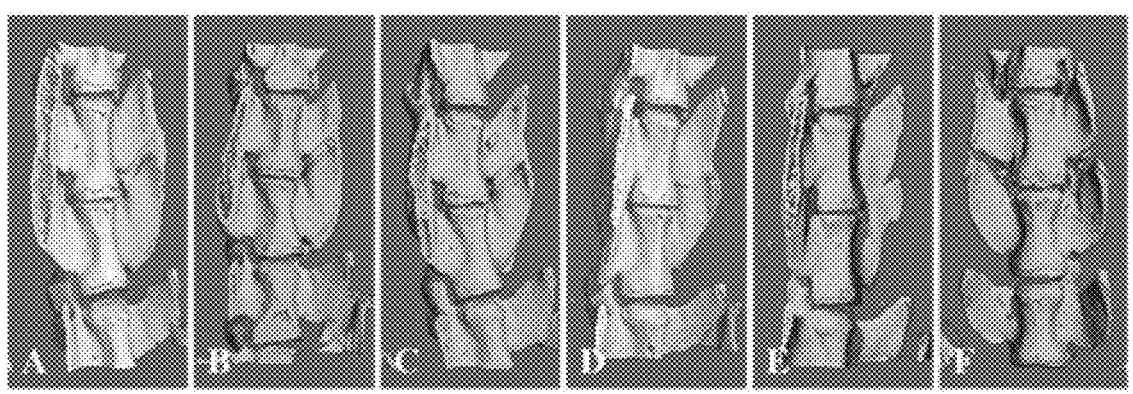
FIG. 20A  FIG. 20B  FIG. 20C  FIG.20D  FIG. 20E  FIG.20F
*FIG. 21*
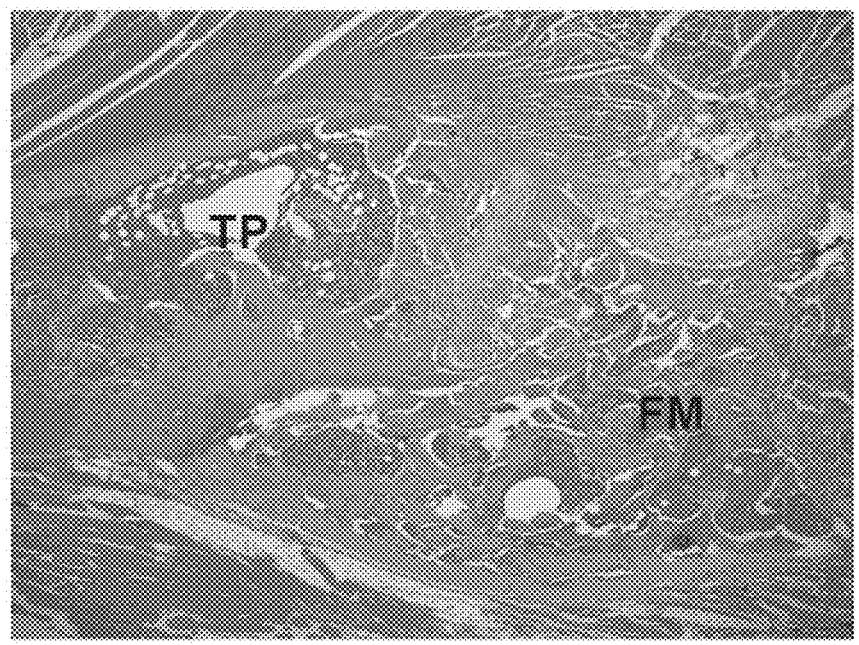

SEQUENCE LISTING

<160> NUMBER OF SEQ ID NOS: 33

<210> SEQ ID NO 1
<211> LENGTH: 19
<212> TYPE: PRT
<213> ORGANISM: Bos sp.

<400> SEQUENCE: 1

Cys Arg Ser Thr Val Arg Met Ser Ala Glu Gln Val Gln Asn Val Trp
1               5                   10                  15

Val Arg Cys

<210> SEQ ID NO 2
<211> LENGTH: 57
<212> TYPE: DNA
<213> ORGANISM: Bos sp.
<220> FEATURE:
<221> NAME/KEY: CDS
<222> LOCATION: (1)..(57)

<400> SEQUENCE: 2 tgc aga agc acc gtg cgg atg tct gct gaa cag gtg cag aac gtg tgg      48
Cys Arg Ser Thr Val Arg Met Ser Ala Glu Gln Val Gln Asn Val Trp
1               5                   10                  15 gtt cgc tgc                                                          57
Val Arg Cys <210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ile Gln Glu Thr Thr Cys Arg Arg Glu Ser Glu Ala Asp Pro Ala Thr
1               5                   10                  15

Cys Asp Phe Gln Arg Gly Tyr His Val Pro Val Ala Val Cys Arg Ser
            20                  25                  30

Thr Val Arg Met Ser Ala Glu Gln Val
        35                  40

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Glu Pro Leu Tyr Glu Pro Ser Arg Glu Met Arg Arg Asn
1               5                   10                  15

<210> SEQ ID NO 5
<211> LENGTH: 200
<212> TYPE: PRT
<213> ORGANISM: Bos sp.

<400> SEQUENCE: 5

Met Ala Met Lys Met Leu Val Ile Phe Val Leu Gly Met Asn His Trp
1               5                   10                  15

Thr Cys Thr Gly Phe Pro Val Tyr Asp Tyr Asp Pro Ala Ser Leu Lys

```
                    20                  25                  30
        Glu Ala Leu Ser Ala Ser Val Ala Lys Val Asn Ser Gln Ser Leu Ser
                 35                  40                  45

Pro Tyr Leu Phe Arg Ala Phe Arg Ser Ser Val Lys Arg Val Asn Ala
         50                  55                  60

Leu Asp Glu Asp Ser Leu Thr Met Asp Leu Glu Phe Arg Ile Gln Glu
         65                  70                  75                  80

Thr Thr Cys Arg Arg Glu Ser Glu Ala Asp Pro Ala Thr Cys Asp Phe
                         85                  90                  95

Gln Arg Gly Tyr His Val Pro Val Ala Val Cys Arg Ser Thr Val Arg
                    100                 105                 110

Met Ser Ala Glu Gln Val Gln Asn Val Trp Val Arg Cys His Trp Ser
                115                 120                 125

Ser Ser Ser Gly Ser Ser Ser Glu Glu Met Phe Phe Gly Asp Ile
        130                 135                 140

Leu Gly Ser Ser Thr Ser Arg Asn Ser Tyr Leu Leu Gly Leu Thr Pro
        145                 150                 155                 160

Asp Arg Ser Arg Gly Glu Pro Leu Tyr Glu Pro Ser Arg Glu Met Arg
                        165                 170                 175

Arg Asn Phe Pro Leu Gly Asn Arg Arg Tyr Ser Asn Pro Trp Pro Arg
                    180                 185                 190

Ala Arg Val Asn Pro Gly Phe Glu
                    195                 200

<210> SEQ ID NO 6
<211> LENGTH: 25
<212> TYPE: PRT
<213> ORGANISM: Homo sapiens

<400> SEQUENCE: 6

Phe Pro Leu Ala Asp His Leu Asn Ser Thr Asn His Ala Ile Val Gln
1               5                   10                  15

Thr Leu Val Asn Ser Val Asn Ser Lys
            20                  25

<210> SEQ ID NO 7
<211> LENGTH: 25
<212> TYPE: PRT
<213> ORGANISM: Homo sapiens

<400> SEQUENCE: 7

Phe Pro Val Tyr Asp Tyr Asp Pro Ala Ser Leu Lys Glu Ala Leu Ser
1               5                   10                  15

Ala Ser Val Ala Lys Val Asn Ser Gln
            20                  25

<210> SEQ ID NO 8
<211> LENGTH: 19
<212> TYPE: PRT
<213> ORGANISM: Bos sp.

<400> SEQUENCE: 8

Cys Asp Ile His Val Leu Lys Gln Asp Gly Gln Phe Ser Val Leu Phe
1               5                   10                  15

Thr Lys Cys

<210> SEQ ID NO 9
<211> LENGTH: 18
```

```
<212> TYPE: PRT
<213> ORGANISM: Homo sapiens

<400> SEQUENCE: 9

Cys Val Ala Val Trp Arg Lys Asn Asp Glu Asn Ile Thr Leu Glu Thr
1               5                   10                  15

Val Cys

<210> SEQ ID NO 10
<211> LENGTH: 19
<212> TYPE: PRT
<213> ORGANISM: Bos sp.

<400> SEQUENCE: 10

Cys Arg Ser Thr Val Arg Met Ser Ala Glu Gln Val Gln Asn Val Trp
1               5                   10                  15

Val Arg Cys

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (6)..(6)
<223> OTHER INFORMATION: Any semi-conservative amino acid
<220> FEATURE:
<221> NAME/KEY: MOD_RES
<222> LOCATION: (7)..(7)
<223> OTHER INFORMATION: Any conservative amino acid
<220> FEATURE:
<221> NAME/KEY: MOD_RES
<222> LOCATION: (9)..(11)
<223> OTHER INFORMATION: Any semi-conservative amino acid
<220> FEATURE:
<221> NAME/KEY: MOD_RES
<222> LOCATION: (13)..(14)
<223> OTHER INFORMATION: Any semi-conservative amino acid
<220> FEATURE:
<221> NAME/KEY: MOD_RES
<222> LOCATION: (16)..(16)
<223> OTHER INFORMATION: Any semi-conservative amino acid
<220> FEATURE:
<221> NAME/KEY: MOD_RES
<222> LOCATION: (17)..(18)
<223> OTHER INFORMATION: Any conservative amino acid

<400> SEQUENCE: 11

Cys Arg Ser Thr Val Xaa Xaa Ser Xaa Xaa Xaa Val Xaa Xaa Val Xaa
1               5                   10                  15

Xaa Xaa Cys

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: modified_base
<222> LOCATION: (25)..(33)
<223> OTHER INFORMATION: a, c, t, g, unknown or other
```

```
<220> FEATURE:
<221> NAME/KEY: modified_base
<222> LOCATION: (37)..(42)
<223> OTHER INFORMATION: a, c, t, g, unknown or other
<220> FEATURE:
<221> NAME/KEY: modified_base
<222> LOCATION: (46)..(48)
<223> OTHER INFORMATION: a, c, t, g, unknown or other

<400> SEQUENCE: 12
tgcagaagca ccgtgnnnyy ytctnnnnnn nnngtgnnnn nngtgnnntt tttttgc      57

<210> SEQ ID NO 13
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Ala or Val

<400> SEQUENCE: 13

Cys Arg Ser Thr Val Lys Val Ser Xaa Gln Gln Val Gln Gly Val His
1               5                   10                  15

Ala Arg Cys

<210> SEQ ID NO 14
<211> LENGTH: 57
<212> TYPE: DNA
<213> ORGANISM: Homo sapiens

<400> SEQUENCE: 14
tgcagaagca ccgtgaaggt atctgcccag caggtgcagg gcgtgcatgc tcgctgc      57

<210> SEQ ID NO 15
<211> LENGTH: 19
<212> TYPE: PRT
<213> ORGANISM: Sus sp.

<400> SEQUENCE: 15

Cys Arg Ser Thr Val Gln Ile Ser Ala Glu Lys Val Gln Asp Val Trp
1               5                   10                  15

Val Arg Cys

<210> SEQ ID NO 16
<211> LENGTH: 57
<212> TYPE: DNA
<213> ORGANISM: Sus sp.

<400> SEQUENCE: 16
tgcagaagca ccgtgcagat atctgctgag aaggtgcagg atgtgtgggt gcgttgt      57

<210> SEQ ID NO 17
<211> LENGTH: 19
<212> TYPE: PRT
<213> ORGANISM: Ovis sp.

<400> SEQUENCE: 17

Cys Arg Ser Thr Val Arg Met Ser Ala Glu Arg Val Gln Asp Val Trp
1               5                   10                  15

Val Arg Cys

<210> SEQ ID NO 18
<211> LENGTH: 57
```

-continued

```
<212> TYPE: DNA
<213> ORGANISM: Ovis sp.

<400> SEQUENCE: 18
tgcagaagca ccgtgcggat gtctgctgaa cgcgtgcagg acgtgtgggt tcgctgc         57

<210> SEQ ID NO 19
<211> LENGTH: 19
<212> TYPE: PRT
<213> ORGANISM: Rattus sp.

<400> SEQUENCE: 19

Cys Arg Ser Thr Val Gln Met Ser Lys Gly Gln Val Lys Asp Val Trp
1               5                   10                  15

Ala His Cys

<210> SEQ ID NO 20
<211> LENGTH: 57
<212> TYPE: DNA
<213> ORGANISM: Rattus sp.

<400> SEQUENCE: 20
tgcaggagca cagtgcagat gtccaaggga caggtgaagg atgtgtgggc tcactgc         57

<210> SEQ ID NO 21
<211> LENGTH: 19
<212> TYPE: PRT
<213> ORGANISM: Mus sp.

<400> SEQUENCE: 21

Cys Arg Ser Thr Val Gln Met Ser Lys Gly Gln Val Lys Asp Val Trp
1               5                   10                  15

Ala His Cys

<210> SEQ ID NO 22
<211> LENGTH: 57
<212> TYPE: DNA
<213> ORGANISM: Mus sp.

<400> SEQUENCE: 22
tgcaggagca ctgtgcagat gtccaaggga caggtaaagg atgtgtgggc tcactgc         57

<210> SEQ ID NO 23
<211> LENGTH: 19
<212> TYPE: PRT
<213> ORGANISM: Gallus sp.

<400> SEQUENCE: 23

Cys Lys Ser Val Val Glu Val Ser Ser Glu Gln Ile Val Asn Val Ile
1               5                   10                  15

Val Arg Cys

<210> SEQ ID NO 24
<211> LENGTH: 57
<212> TYPE: DNA
<213> ORGANISM: Gallus sp.

<400> SEQUENCE: 24
tgcaaaagcg ttgtagaagt ctccagtgag cagattgtga atgttattgt gcgatgc         57

<210> SEQ ID NO 25
<211> LENGTH: 19
```

```
<212> TYPE: PRT
<213> ORGANISM: Salmo sp.

<400> SEQUENCE: 25

Cys Thr Ala Arg Val Arg Val Thr Ala Glu Phe Thr Gln Val Val Ser
1               5                   10                  15

Leu Asn Cys

<210> SEQ ID NO 26
<211> LENGTH: 57
<212> TYPE: DNA
<213> ORGANISM: Salmo sp.

<400> SEQUENCE: 26
tgcaccgcac gtgttcgcgt cactgcagag ttcactcagg ttgtgtccct gaactgt       57

<210> SEQ ID NO 27
<211> LENGTH: 19
<212> TYPE: PRT
<213> ORGANISM: Salmo sp.

<400> SEQUENCE: 27

Cys Thr Ala Arg Val Arg Val Thr Ala Glu Leu Thr Gln Val Val Ser
1               5                   10                  15

Leu Asn Cys

<210> SEQ ID NO 28
<211> LENGTH: 57
<212> TYPE: DNA
<213> ORGANISM: Salmo sp.

<400> SEQUENCE: 28
tgcaccgcac gtgttcgtgt cactgcagag ctcactcagg ttgtgtccct gaactgt       57

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Ser Glu Ala Asp Pro Ala Thr Cys Asp Phe Gln Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Asn Ser Gln Ser Leu Ser Pro Tyr Leu Phe Arg
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Ser Arg Gly Glu Pro Leu Tyr Glu Pro Ser Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ser Tyr Leu Leu Gly Leu Thr Pro Asp Arg
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Tyr His Val Pro Val Ala Val Cys Arg
1               5                   10
```

ENHANCEMENT OF BONE MORPHOGENIC PROTEIN (BMP) RETENTION WITH BMP BINDING PEPTIDE (BBP)

This work was supported by the U.S. Department of Veterans Affairs, and the Federal Government has certain rights in this invention.

FIELD OF THE INVENTION

The invention relates to the binding and retention of bone morphogenic proteins ("BMPs") by growth factors (including BMP Binding Peptide ("BBP")) resulting in prolonged exposure of BMP to the desired site of action, and in earlier and greater mesodermal stem cell proliferation, chondrogenesis, osteogenesis and/or calcification, including at a fusion or repair site.

BACKGROUND OF THE INVENTION

The use of autogenous bone graft is the current gold standard in the 1.5 million bone-grafting surgeries performed annually in the United States. Although this practice has resulted in high rates of fusion success, it is associated with increased operative time and blood loss, along with a significant degree of donor-site morbidity. Additionally, in certain settings such as revision cases, multilevel constructs, or in patients with medical comorbidities, autogenous bone graft may exist in limited quantity and quality. This significant need for a suitable alternative to autogenous bone graft has stimulated great interest in the exploration of bone graft substitutes and extenders.

One avenue of extensive research involves the use of bone morphogenetic proteins (BMP). BMPs are osteoinductive proteins in the superfamily of transforming growth factor-beta (TGF-β). Since their discovery, several BMPs have been identified and are currently being produced in mass quantities using recombinant technologies. Recombinant human osteogenic protein-1 (rhOP-1), also known as rhBMP-7, and rhBMP-2 are the only two BMPs currently approved for orthopedic procedures. Both have shown to be effective osteoinductive proteins in preclinical and clinical trials. These growth factors provide a potential alternative to autogenous bone graft and are capable of overcoming the suboptimal biological environment for bone formation seen in revision surgeries and in patients with risk factors for psuedoarthrosis. Unfortunately, the utility of these alternatives is limited by their cost, and associated risks, such as local inflammatory reactions, ectopic bone formation, and the theoretical risks of carcinogenicity, and teratogenicity. The risk for these adverse factors increase in a dose-dependant manner and are present at the doses currently used for orthopedic procedures.

Growth factors are substances, including peptides, which affect the growth and differentiation of defined cell populations in vivo or in vitro. Normal bone formation occurs during development, bone remodeling occurs in adult life, and bone repair occurs in order to preserve the integrity of the skeleton. Bone formation, remodeling and repair involve bone resorption by osteoclasts and bone formation by osteoblasts. Cell differentiation and the activity of osteoblasts and osteoclasts are regulated by growth factors. Thus, any interference between the balance in cell differentiation and resorption can affect bone homeostasis, bone formation and repair.

The induction of ectopic bone formation by demineralized bone matrix (DBM) has been described. Further, the properties of the partially purified protein fraction, including BBP have been described. BBP is a synthetic, cyclic, 19 amino acid peptide. The sequence for this peptide is based on that of a portion of a 18.5 kD protein called "bone morphogenetic protein/noncollagenous protein" (BMP/NCP) which had no independent osteogenic activity. This protein was found to be identical to a fragment of a previously isolated protein, spp24 (secreted phosophoprotein 24 kD). Spp24 shares with other BMP binding proteins, such as fetuin, a cystatin domain which in turn contains a smaller motif, the TRH-1 (TGF-β receptor II homology 1) domain. Spp24 binds to BMP-2 and has been shown to inhibit its osteogenic activity in an ectopic bone formation model and in a transgenic model of bone formation.

Safe, effective and affordable compositions, devices and methods are desired to enhance bone formation and repair, including treatment of bone disorders (such as osteoporosis), bone injury (such as fracture healing of flat (e.g., membranous) and long (e.g., endochondral) bones, non-union fractures and reconstructive surgery), sites of knee/hip/joint repair or replacement surgery treating periodontitis, periodontal regeneration, alveolar ridge augmentation for tooth implant reconstruction, for example.

BRIEF SUMMARY OF INVENTION

The inventions relate to the binding and retention of TGF-β superfamily member, such as BMPs, by growth factors (including BBP) resulting in prolonged exposure of TGF-β superfamily member(s) to the desired site of action. In one embodiment, this will lead to earlier and greater mesodermal stem cell proliferation, chondrogenesis, osteogenesis and/or calcification rates, including bone fusion or repair. For example, BBP has been disclosed as enhancing ossification caused by recombinant BMP. Further, BBP as used with BMP in vivo causes osteogenesis to occur faster, to a greater extent and with smaller amounts of rhBMP-2.

The inventions are related to the retention of growth factors at the desired site of action. In one embodiment, the invention relates to the use of BBP to bind and retain members of the TGF-β superfamily member, including BMPs and related growth factors. In one embodiment of the invention, BBP may be used to retain rhBMP-2.

The inventions are related to increasing the speed and/or degree of osteogeneis and/or calcification by growth factors due to the retention of the growth factor at the site of action. In one embodiment, the invention relates to the use of BBP increase the speed and/or degree of chondrogeneisis, osteogeneis and/or calcification by members of the BMP family and related growth factors. In one embodiment of the invention, BBP may be used to increase the speed and/or degree of osteogeneis and/or calcification by rhBMP-2.

The inventions are related to the retention of growth factors at the site resulting from the association of the BMPs with BBP. The equilibrium constants and/or dissociation constants may result in the desired binding and retention of growth factors by BBP.

Compositions and substrates including factors which bind growth factors, such as BBP, and methods of using these substances which associate with growth factors are useful. Applications include preventing the diffusion from, or maintaining the concentration of growth factors at the site of action, such as the site of bone repair.

The invention may include a method of treatment with agents for associating with growth factors to maintain desirable concentrations of growth factors at the cite of action.

In one application of the invention, the method may be applied to induce bone formation or repair.

The invention may also include implants having agents for associating with growth factors and/or seeded with pluripotential or differentiated cells. In one application BBP, TGF-β superfamily member(s) (such as BMP) and cells may be selected for inducing bone formation or repair. The invention may also include the application of agents for associating with growth factors at a desired site of action. Implants may include, but are not limited to pins, screws and plates that are used to immobilize fractures, enhance bone formation or stabilize a prosthetic implant by stimulating bone formation or repair.

This invention is advantageous at least in that BBP enhances the rate and/or degree of activity by the selected growth factor, such as BMPs. Further, this invention is advantageous at least in that BBP acts synergistically with TGF-β family members, such the a lower amount of TGF-β family member is effective to achieve the same or a greater rate or degree of growth than expected with the TGF-β family member alone. Thus, the combination can improve the time to clinical benefit, improve the clinical outcome, reduce unwanted side effects and decrease the dose of growth factor used (and attendant cost of treatment).

In one embodiment, a delivery system would provide a sustained local concentration of BMP sufficient to induce bone formation or repair, while minimizing the concentration of BMP used, and any local or systemic side effects.

In one embodiment a combination of BBP and at least one TGF-β family member (such as OP-1) may be used to reduce the cost associated with the use of growth factors in bone related applications, reduce side effects affiliated with of high doses of growth factors (such as for BMPs, significant swelling and ectopic bone formation) and improve clinical outcomes by utilizing a combination of BBP with OP-1. Thus, in one aspect of the invention, BBP may be used to bind BMPs and other members of the TGF-β family, and slowly releases the growth factors at the desired site of action. For example, the use of BBP in conjunction with rhOP-1 may be used to generate significantly earlier and greater spinal fusion.

These, as well as other objects, features and benefits will now become clear from a review of the following detailed description of illustrative embodiments and the accompanying drawings.

BRIEF DESCRIPTION OF DRAWINGS

FIG. 1A are BBP bovine (1) amino acid and (2) nucleic acid sequences, respectively; FIG. 1B is a partial amino acid sequence of the bovine BMP binding protein ("BBP") showing the cystatin homology region, the BMP-2 homology region, and the TGF-β receptor II homology domain.

FIG. 2 is an amino acid sequence alignment of human BMP-2 and the BMP-2 homology region in bovine SPP-24; (i, identical; c, conservative substitution; sc, semi-conservative substitution).

FIG. 3 is an amino acid sequence alignment of bovine fetuin and human TGF-β receptor II (above) and of human TGF-β receptor II and the TGF-β receptor II homology domain of bovine SPP-24 (corresponding to BBP) (bottom); (i, identical; c, conservative substitution; sc, semi-conservative substitution).

FIG. 10 is a bar graph depicting the percentage of rhBMP-2 retention over 1, 3 and 7 days in the presence or absence of BBP.

FIG. 11 includes amino acid sequences against which specific SSP-24/BBP antibodies have been generated.

FIGS. 12 A & 12B depict flowcharts of exemplary methods of the invention.

FIGS. 13 A & 13B are schematic depictions of two embodiments of the invention.

FIGS. 14 A is a chart showing the amino acid sequences for BPP in various species. FIG. 14 B is a list of the nucleic acid sequences for BPP in various species.

(FIG. 19A) demonstrates a successful arthrodesis with a large intertransverse osseous fusion at L4-L5 whereas (FIG. 19B) shows a nonunion at L4-L5.

FIGS. 20A-20F are three-dimensional reconstruction of microcomputerized tomographic images of rat spines (cut-plane images). Fused spines from (FIG. 20A) Group IV (10 µg rhOP-1), (FIG. 20B) Group V (3 µg rhOP-1), (FIG. 20C) Group VI (3 µg rhOP-1+BBP), (FIG. 20D) Group VII (1 µg rhOP-1), (FIG. 20E) Group VIII (1 µg rhOP-1+BBP). (FIG. 20F) Example of nonunion seen in Group VIII.

FIG. 21 is histological section from a successful fusion from Group VI (3 µg rhOP-1+BBP) showing a large fusion mass (FM) with much mature bone and extensive remodeling of the transverse process (TP). Original magnification 25×.

DETAILED DESCRIPTION OF ILLUSTRATIVE EMBODIMENTS

Figure 4:
FIG. 4 is a radiogram of mouse hind quarters 21 days after implantation of 500 µg of BBP in atelocollagen (top) or atelocollagen alone (bottom).

One embodiment of the invention comprises a peptide having the amino acid sequence of SEQ ID No: 1a. The bovine derived amino acid SEQ ID No: 1a has been designated BBP, and SEQ ID No: 1 b corresponds to the bovine nucleic acid sequence encoding BBP.

One embodiment of the invention comprises a peptide having the amino acid sequence of SEQ ID No. 12a, which is the sequence of human BBP. SEQ ID No. 12b corresponds to the human nucleic acid sequence encoding human BBP.

BBP is a 19 amino acid, 2.1 kD peptide, derived from a 18.5 kD fragment of a known 24 kDa secreted phosphoprotein ("SPP-24"). SPP-24 is illustrated by SEQ ID No: 2. BBP contains the cystatin-like domain of SPP-24.

The BBP amino acid sequence is similar to the TGF-β/BMP-binding region of fetuin, a member of the cystatin family of protease inhibitors. BBP binds rhBMP-2 (recombinant human BMP-2), and also binds other molecules having similar binding domains to BMP-2, such as other TGF-β super family members (including but not limited to BMP-4, BMP-7, TGF-β and GDF-5) and affects their retention rates and/or activity. However, any growth factor may be useful in this invention to the extent it binds BBP with a suitable equilibrium and/or dissociation constant to be bound and retained by BBP for a greater period of time than without the presence of BBP.

BBP alone induces calcification of vertebrate chondrogenic and osteogenic precursor cells. BBP increases the increases the rate and degree to which rhBMP-2 induces bone formation. Surprisingly, BBP acts synergistically with BMP-2 in vivo causes mesodermal stem cell proliferation, chondrogenesis, osteogenesis and/or calcification to occur faster and to a greater extent and with smaller amounts of rhBMP-2.

For example, when implanted alone in mouse muscle, the BBP induces dystrophic calcification. The process of bone formation in repair or ectopic bone formation the "mouse hindquarter" or "muscle pouch" model recapitulates endochondral bone formation. The first step involves the production of cartilage, which is replaced by bone. This same process that occurs during endochondral bone formation in development, while some membranous bone formation occurs directly without a cartilage intermediary.

In one embodiment of the invention, a peptide comprising a fragment of BBP may be useful, if the fragment similarly increases degree or rate of mesodermal stem cell proliferation, chondrogenesis, osteogenesis and/or calcification by BMP-2 in mammalian cells, or increases degree or rate of calcification in vertebrate cells, or specifically mammalian chondrogenic or osteogenic progenitor cells.

Forms of BBP having modifications of the amino acid sequences disclosed herein may also be useful in this invention, so long as the TGF-β binding region maintains sufficient sequence and structure to bind TGF-β family members with a suitable equilibrium and/or dissociation constant to be effective to retain them at the cite of action for a greater amount of time than if no BBP was present.

For example, the conserved amino acid sequences of BBP between species, deletional or insertional modifications, conservative or semi-conservative substitutional modifications are intended to be encompassed in the claimed BBP, to the extent that the modified amino acid sequences increase the residency time and or activity of BMP-2 or other TGF-β homologous molecules. BBP is a β-pleated sheet-turn-beat pleated sheet molecular motif ("B-T-B"). It is currently believed that growth factor binding amino acids reside in the T-section. Therefore, amino acid substitutions in the T-section may affect activity of BBP to a greater extent than substitutions in the B regions.

One embodiment of the invention comprises a peptide having the sequence of SEQ ID No. 11: C-R-S-T-V-X-Y-S-X-X-X-V-X-X-V X-Y-Y-C, which is the mammalian consensus sequence for BBP. FIG. 14A shows the homology in amino acid sequence across bovine (SEQ ID No. 1; nucleic acid sequence set forth at SEQ ID No. 2), human (SEQ ID No. 13; nucleic acid sequence set forth at SEQ ID No. 14 (position 9 is either A or V), porcine (SEQ ID No. 15; nucleic acid sequence set forth at SEQ ID No. 16), ovine (SEQ ID No. 17; nucleic acid sequence set forth at SEQ ID No. 18), rat (SEQ ID No. 19; nucleic acid sequence set forth at SEQ ID No. 20), and mouse (SEQ ID No. 21; nucleic acid sequence set forth at SEQ ID No. 22) BBP. FIG. 14A also shows highly conserved regions in chicken (SEQ ID No. 23; nucleic acid sequence set forth at SEQ ID No. 24), salmon (SEQ ID No. 25; nucleic acid sequence set forth at SEQ ID No. 26) and trout (SEQ ID No. 27; nucleic acid sequence set forth at SEQ ID No. 28).

In FIG. 14 A, "X" and "Y" are used to denote amino acid substitutions that are understood to be semi-conservative or conservative, respectively. Conservative substitutions include amino acids selected from the same group, and semi-conservative substitutions include substitutions that are not believed to affect the BMP-2 binding domain or the function of the BBP. For example, the substitution at position 6 is conservative between human, rat and ovine, but semi-conservative with some other species because the amino acids reported at that position in different species are: Q and E (Q in porcine, rat, and mouse BBP, and E in chicken). Although K and R are both classified as basic amino acids, Q is classified as an uncharged polar amino acid, therefore the substitution is not conservative. The substitution is semi-conservative, however, because the function of BBP is believed to be unaffected. Semi-conservative substitutions are also found at positions 9, 10, 11, and 16. At position 9, the amino acids A is found in bovine, human, porcine and ovine BBP, compared to K in rat and mouse BBP. At position 10, the amino acid E is reported for bovine, porcine, and ovine BBP, human BBP contains Q at that position, and rat and mouse BBP contain the amino acid G. At position 11, the amino acid Q is found in bovine, human, rat and mouse, whereas K, is reported for porcine BBP and R for ovine BBP. At position 16, W is found in bovine, porcine, ovine, rat and mouse BBP, whereas human BBP contains an H. There are also semi-conservative substitutions at positions 13 and 14 between rat/human, as opposed to other species.

An example of a conservative substation is found at position 7. At this position, different hydrophobic amino acids are observed in different species, namely, M in bovine, ovine, rat, and mouse BBP, compared to V in human and I in porcine BBP. This substitution is considered conservative because M, V, and I are all hydrophobic amino acids. Other conservative substitutions occur at positions 17 and 18. Two hydrophobic amino acids, A and V, are found at position 17. At position 18, two basic amino acids, R and H, are found.

One embodiment of the invention may be a composition including BBP which increases degree or rate of calcification in vertebrate cells, or more specifically mammalian chondrogenic or osteogenic precursor cells. Further, the invention may be including BBP which increases degree or rate of osteogenesis by BMP-2, and one of BMP-2 or demineralized bone matrix. Further, the composition may additionally or alternatively include other TGF-β family members, including but not limited to BMP-4, BMP-7, TGF-β and GDF-5. It is further noted that other TGF-β family members are involved in immune system function, and BBP may bind with an effect the residence time or activity of those molecules, as well which may effect immune function, inflammation or tumor growth.

In one embodiment, the invention may include a medicament for use in inducing the rate or degree of osteogenesis in a vertebrate including a therapeutically effective dosage of BBP and BMP or DBM. The invention may further include, a medicament for use in inducing the rate or degree of calcification in a vertebrate including a peptide comprising BBP.

Applications for BBP. A number of applications for BBP are suggested from its pharmacological (biological activity) properties. For example, BBP alone or in combination with other TGF-family members such as BMP-2, BMP-4, BMP-7, GDF-5, or demineralized bone matrix may be used in clinical or research methods for inducing bone formation, maintaining bone homeostasis and/or enhancing bone repair. BBP may be used alone or in combination to treat developmental or homeostatic bone disorders (such as osteoporosis), bone injury (such as fracture healing flat (e.g., membranous) and long (e.g., endochondral) bones, non-union fractures and reconstructive surgery. The invention may also be used in treating periodontitis, periodontal regeneration, alveolar ridge augmentation for tooth implant reconstruction, treatment of non-union fractures, sites of knee/hip/joint repair or replacement surgery.

Clinical indices of a method or compounds ability to maintain bone homeostasis is evidenced by improvements in bone density at different sites through out the body as assessed, at least by DEXA scanning. Enhanced bone formation in a healing fracture is routinely assessed by regular X-ray of the fracture site at selected time intervals. More advanced techniques for determining the above indices, such as quantitative CT scanning or quantitative histological methods (eg., tissue is processed, stained, and microscopically examined and bone defined an measured with image analysis) may be used. Further, measures of bone density, bone area, bone mineral content, formation of ectopic bone, and increases in the opacity of tissue upon X-ray examination, expression of alkaline phosphatase activity, calcium incorporation, mineralization or expression of osteocalcin mRNA may be used to observe the effects of BBP calcification and/or osteogenesis The invention may also include the use of agents which inhibit osteoclastic bone resorption. Agents which may be useful in this invention to effect osteoclastic bone resorption include, but are not limited to, bisphosphonates, the selective estrogen receptor modulators, calcitonin, and vitamin D/calcium supplementation. The invention may also include the use of agents which induce osteoblastic bone formation. Agents which may be useful in this invention include, but are not limited to PTH, sodium fluoride and growth factors, such as insulin-like growth factors I and II.

The in vivo models used to show the calcification effects of BBP alone or osteogenic effects in combination with BMP have been used previously in demonstrating similar behaviors of other compounds. In particular, in vivo models have also previously been able to successfully predict the in vivo osteogenic effects of compounds such as BMP and insulin like growth factors (IGF). Specifically, it has been demonstrated that the osteogenic effects of BBP in an animal model using rat femur, ectopic bone formation model. Therefore it is anticipated that, based on these similar findings, BBP will have osteogenic effects in vivo in humans.

Therapeutically Effective Dose. A therapeutically effective dose of BBP or a TGF-β family member useful in this invention is one which has a positive clinical effect on a patient or desired effect in cells as measured by the ability of the agent to enhance mesodermal stem cell proliferation, chondrogenesis, osteogenesis and/or calcification, as described above. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

This invention is advantageous in at least the dosage of BMP-2 required to induce a given rate or degree of osteogenesis may be reduced when BMP-2 is combined with BBP. Thus, BBP and the TGF-β family members act synergistically.

Dosage Form. The therapeutically effective dose of an agent included in the dosage form may be selected by considering the type of agent selected and the route of administration. The dosage form may include a agent in combination with other inert ingredients, including adjutants and pharmaceutically acceptable carriers for the facilitation of dosage to the patient, as is known to those skilled in the pharmaceutical arts.

Therapeutic formulations of BBP (when claimed is intended to include modifications or fragments thereof), may be prepared for storage by mixing the BBP having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or poly(ethylene glycol) (PEG).

The dosage form may be provided in preparations for subcutaneous (such as in a slow-release capsule), intravenous, intraparitoneal, intramuscular, peri- or intraskeletal for example. Any one or a combination of agents may be included in a dosage form. Alternatively, a combination of agents may be administered to a patient in separate dosage forms. A combination of agents may be administered concurrent in time such that the patient is exposed to at least two agents for treatment.

Additional Agents. The invention may include treatment with an additional agent which acts independently or synergistically with BBP to enhance calcification osteogenesis. For example, BBP may be combined with BMP, bisphosphonates, hormone therapy treatments, such as estrogen receptor modulators, calcitonin, and vitamin D/calcium supplementation, PTH (such as Forteo or teriparatide, Eli Lilly, sodium fluoride and growth factors that have a positive effect on bone, such as insulin-like growth factors I and II and TGF-β. Those skilled in the art would be able to determine the accepted dosages for each of the therapies using standard therapeutic dosage parameters, or reduced dosages where the effects of BBP are synergistic with the secondary agent, such as BMPs.

BBP is currently thought to act upon BMP-2 at least by increasing its residency time with a substrate. One embodiment of the invention is a method of detecting the ability of BBP to enhance the residency time of a TGF-β homologous molecule including applying an amount of the TGF-β homologous molecule at a first and second selected location. Further, applying a selected amount of BBP at the first selected location, and finally detecting the amount of the TGF-β homologous molecule at the first and second location after a selected time period; and calculating the difference between the amount of the TGF-β homologous molecule at the first and second location.

In one embodiment, the invention may include a method of enhancing the rate or degree of mesodermal stem cell proliferation, chondrogenesis, osteogenesis and/or calcification in vertebrate tissue including application of BBP which increases degree or rate of osteogenesis by BMP-2 in mammalian cells and one of a TGF-β family member, such as BMP-2 or demineralized bone matrix.

In one embodiment, the invention may include a method of enhancing the rate or degree of mesodermal stem cell proliferation, chondrogenesis, osteogenesis and/or calcification in vertebrate tissue including administering chondrogenic or osteogenic precursor cells to the patient at a location proximate to the desired location of osteogenesis; further, administering BBP, and administering one of a TGF-β family member, such as BMP-2 or demineralized bone matrix.

In one embodiment, the invention may include a method of enhancing the rate or degree of osteogenesis in a vertebrate including treating vertebrate mesynchymal stem cells with one of a TGF-β family member, such as BMP-2 or demineralized bone matrix to induce osteogenesis of the cells. Further, treating the vertebrate mesynchymal stem cells with BBP; and administering the vertebrate mesynchymal stem cells to the patient at a location proximate to the desired site of action.

For example, mammalian cells, such as mesenchymal stem cells can be harvested, from the patient or a cell donor. The cells may be injected in a location where bone formation or repair is desired (such as a fracture site or implant site), or first treated with BBP and/or BMP. The cells may then be re-administered to the patient, either systemically or at a selected site. Additionally, the patient may by treated locally or systemically with at least one additional agent which effects mesodermal stem cell proliferation, chondrogenesis, osteogenesis and/or calcification.

FIGS. 12A and B depict flowcharts of exemplary methods of the invention, the steps of which may be performed in any order.

One embodiment of the invention may include an article of manufacture comprising BBP immobilized on a solid support. The solid support may further include a TGF-β family member, such as a BMP family member, including BMP-2, or demineralized bone matrix.

One embodiment of the invention may include an implant for use in vivo including, a substrate where at least the surface of the implant includes BBP. The implant may further include MSC, chondrocytic or osteoblastic progenitor cells. Further, the implant may be formed into the shape of a pin, screw, plate, or prosthetic joint, for example.

For example, FIGS. 13A & B depict two embodiments of the present invention. In FIG. 13A, the invention may include implants or grafts (200) for use in the body comprising, a substrate having a surface (201), wherein at least the surface of the implant includes BBP (203) in an amount sufficient to induce, calcification or osteogenesis in the surrounding tissue. The implant may include mesynchymal stem cell, chondrogenic or osteogenic cells expressing BBP, and/or BMP-2, demineralized bone matrix, or collagen cultures. The implant may be in the form of, but are not limited to pins, screws, plates or prosthetic joints which may be placed in the proximity of or in contact with a bone (202) that are used to immobilize a fracture, enhance bone formation, or stabilize a prosthetic implant by stimulating formation or repair of a site of bone removal, fracture or other bone injury (204).

As shown in FIG. 13B, the invention may also include the in vitro (such as on cultures of collagen or chondrocytes) or in vivo application of at a least BBP containing composition or BBP expressing cells (206) in the proximity of or in contact with a bone (202), an implant (200) at a site of bone removal, fracture or other bone injury (204) where osteogenesis and/or calcification is desired. The BBP composition may be applied in combination with other agents such as BMP-2, demineralized bone matrix, or collagen cultures.

For example, the use of stem cells for treating bone related disorders in humans has also been examined. Infusion of osteoblastic progenitor stem cells from a healthy individual into a diseased individual has been shown to improve bone density in these patients (OI). Cells may be pretreated with BMP and BPP, or applied concurrently therewith.

In one embodiment, the invention may include a monoclonal or polyclonal antibody having selective binding to any portion of BBP, or the BBP portion of the BBP precursor, SSP-24.

BBP or fragments thereof may be fused (for example by recombinant expression or in vitro covalent methods) to an immunogenic polypeptide and this, in turn, may be used to immunize an animal in order to raise antibodies against BBP. Antibodies are recoverable from the serum of immunized animals. Alternatively, monoclonal antibodies may be prepared from cells from the immunized animal in conventional fashion. Immobilized antibodies may be useful particularly in the detection or purification of BBP.

Two examples of specific peptide sequences against which rabbit polyclonal antibodies have been generated include: (1) An antibody against the peptide sequence "IQETTCRRESEADPATCDFQRGYHVPVAVCRST-VRMSAEQV" (FIG. 11—SEQ. ID No. 3) that reacts with both bovine and human SSP-24, the BBP precursor. This antibody was generated in rabbits immunized with the synthetic peptide indicated above. Further, (2) An antibody directed against the sequence "CGEPLYEPSREMRRN" (FIG. 11—SEQ. ID No. 4) that was also produced in rabbits immunized with a synthetic peptide corresponding to the indicated sequence. This second antibody reacts with bovine SSP-24. The N-terminal cysteine is not a part of the native SSP-24 sequence; but is preferably included to allow the peptide to be conjugated to chromatographic resins for affinity chromatography. Additional peptide sequences may be identified for specific binding to BBP, and sequences may be selected so as to create an antibody having selective binding with BBP, but so as to not interfere with BBP binding, such as the region of BBP which binds with BMP-2 or other TGF-β family members.

Antibodies against the sequences above, corresponding sequences in the mouse, human, and rat genome, or any derivatives of the immunogenic sequences are also useful in this invention. These antibodies are useful in at least to the extent that they recognize the BBP amino acid sequence with high specificity. Such antibodies may also be useful in inhibiting protein specific interactions of BBP with other molecules where the antibody binds to a location on the peptide which interacts with other molecules. The inhibition of BBP activity in situations where the rate or degree of chondogenesis or osteogenesis may be modified.

In one embodiment the invention, antibodies specific for BBP may be useful in decreasing the degree or rate of osteogenesis by BMP-2 in vertebrate cells or decreasing degree or rate of calcification in vertebrate cells, or more specifically in mammalian chondrogenic or osteoblastic precursor cells.

One embodiment of the invention may also include a method of using BBP selective antibodies to detect the presence of SSP-24/BBP in sample (including but not limited to a cell culture, tissue sample, peptide fraction, Western blot) including exposing the sample to the BBP selective antibody and visualizing the complex of SSP-24/BBP and BBP antibody.

In one embodiment of the invention, BBP antibodies may be used for the affinity purification of the BBP from recombinant cell culture or natural sources. BBP antibodies that do not detectably cross-react with other growth factors can be used to purify BBP from these other family members.

In one embodiment, the invention may include a nucleic acid construct comprising a DNA or RNA nucleic acid sequence encoding BBP, or modified sequences corresponding to the modified amino sequences described above.

The invention may also include, an expression vector operatively linked to a nucleic acid sequence encoding BBP, or precursor SSP-24 Further, a transformant may be obtained by introducing the nucleic acid construct encoding for BBP, or its precursor SSP-24 into a host cell.

Practice of this invention may include the use of an oligonucleotide construct comprising a sequence coding for BBP and for a promoter sequence operatively linked in a mammalian or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. Such cloning vectors are well known to those of skill in the art. Expression vectors, unlike cloning vectors, may contain an inducible or constitutive promoter which is recognized by the host organism and is operably linked to the BBP nucleic acid. The nucleic acid may be operably linked when it is placed into a functional relationship with another nucleic acid sequence. For example, DNA for a pre-sequence or secretory leader is operably linked to DNA for a polypeptide if it is expressed as a pre-protein which participates in the secretion of the polypeptide.

One embodiment of the invention may also include a method of using DNA or RNA nucleic acid sequences complimentary and having specific binding for the DNA or RNA sequences encoding BBP to detect the presence of BBP DNA or RNA in a sample, respectively (including but not limited to a cell culture, tissue sample, nucleic acid fraction, or Southern or Northern blot) including exposing the sample to the complimentary BBP DNA or RNA sequences and visualizing the complex of hybrids.

Example 1

Extraction and Separation of Non-Collagenous Bone Proteins (NPCs)

Methods: NCPs were extracted from defatted, demineralized human cortical bone powder with 4 M GuHCl, 0.5 M $CaCl_2$, 2 mM N-ethylmalemide, 0.1 mM benzamidine HCl, and 2 mM $NaN_3$ for 18 hr at 6° C. Residual collagen and citrate-soluble NCPs were extracted by dialysis against 250 mM citrate, pH 3.1 for 24 hours at 6° C. The residue was pelleted by centrifugation (10,000×g at 6° C. for 30 min), defatted with 1:1 (v/v) chloroform: methanol for 24 hr at 23° C., collected by filtration and dried at 22° C. The material was resuspended in 4 M GuHCl, dialyzed against 4 M GuHCl, 0.2% (v/v) Triton X-100, 100 mM Tris-HCl, pH 7.2 for 24 hr at 6° C., then dialyzed against water, and centrifuged at 10,000×g for 30 min at 6° C. The pellet was lyophilized and subsequently separated by hydroxyapatite chromatography.

Chromatography was conducted using a BioLogic chromatography workstation with a CHT-10 ceramic hydroxyapatite column (BioRad, Hercules, Calif.). Bovine BMP/NCP was solubilized in 6 M urea, 10 mM sodium phosphate, pH 7.4. The sample was loaded onto the hydroxyapatite column and the unbound fraction was collected. Bound proteins were eluted with increasing concentration of sodium phosphate to 300 mM over a linear gradient of five column volumes. Five ml fractions were collected during the course of the run. The fraction which separated at 180 mM phosphate was separated further by SDS-PAGE electrophoresis. A band corresponding to a $M_r$ of 18.5 was excised and submitted for sequence analysis by matrix assisted laser-desorption ionization/time of flight mass spectroscopy (MALDI/TOF MS).

Results: Sequence Identification and Analysis. The fraction of bBMP/NCP which eluted from hydroxyapatite at 180 mM phosphate was separated by SDS-PAGE electrophoresis and the material with a $M_r$ of 18.5 kD was submitted for MALDI/TOF MS analysis. The major protein component of this material was determined to be a fragment of SPP-24 on the basis of six peptides with sequences identical to regions of that protein. (Hu, et al., Isolation and molecular cloning of a novel bone phosphoprotein related in sequence to the cystatin family of thiol protease inhibitors. J. Biol. Chem. 270:431-436, 1995.) The sequences of these peptides are shown in Table 1.

TABLE 1

Identification of the 18.5 kD protein by MALDI/TOF mass spectroscopy and peptide fingerprinting.

| Expected Mass [a] | Observed Mass [a] | Peptide Sequence |
| --- | --- | --- |
| 1526.574 | 1526.53 | ESEADPATCDFQR* (SEQ ID NO: 29) |
| 1411.600 | 1411.71 | VNSQSLSPYLFR (SEQ ID NO: 30) |
| 1291.406 | 1291.41 | SRGEPLYEPSR (SEQ ID NO: 31) |

TABLE 1-continued

Identification of the 18.5 kD protein by MALDI/TOF mass spectroscopy and peptide fingerprinting.

| Expected Mass [a] | Observed Mass [a] | Peptide Sequence |
|---|---|---|
| 1249.409 | 1249.48 | NSYLLGLTPDR (SEQ ID NO: 32) |
| 1158.363 | 1158.27 | GYHVPVAVCR* (SEQ ID NO: 33) |

*modified cystein;
[a] = peptide masses are expressed as [M + H⁺]

Analysis of this sequence with the SWISS-PROT data base revealed the cystatin-like domain which had been previously described, but no other sequence similarities of relevance to bone metabolism. (Hu, et al.) However, it is known from other work that other cystatin-like proteins interact with proteins having a role in bone metabolism. Specially, members of the cystatin family have TGF-β and BMP-2 binding properties based on similarities to the TGF-β receptor. (Brown, et al., Friends and relations of the cystatin superfamily—new members and their evolution.: Protein Sci. 6:5-12, 1997; Demetriou, et al., Fetuin/α2-HS glycoprotein is a transforming growth factor-β type II receptor mimic and cytokine antagonist. J. Biol. Chem. 271: 12755-12761, 1996.) However, fetuin antagonizes BMP activity. (Hu, et al.) Therefore, a manual comparison was made of the cystatin-like region of SPP-24 and the cystatin-like domain of fetuin.

FIG. 1B is a partial amino acid sequence of the bovine SSP-24, the BMP-2 homology region, and the TGF-β receptor II homology domain. Underlined amino acids have been confirmed to be present by mass spectroscopy. (GenBank Accession Number U08018; Hu, et al.)

Two regions of interest were identified in the cystatin-like region of SPP-24. One region had some sequence similarity to BMP-2, whereas the other region had sequence similarity to the TGF-β receptor II homology domain of fetuin. That part of the sequence of SPP-24 which contains these two regions is shown in FIG. 1B.

Comparisons of the two regions of interest to human BMP-2 and human TGF-β receptor II are shown in FIGS. 2 and 3. FIG. 2 is an amino acid sequence alignment of human BMP-2 and the BMP-2 homology region in bovine SPP-24. FIG. 3 is an amino acid sequence alignment of bovine fetuin and human TGF-β receptor II (top) and of human TGF-β receptor II and the TGF-β receptor II homology domain of bovine SPP-24 (corresponding to BBP)(bottom). Alignment of the SPP-24, fetuin, human BMP-2, and human TGF-β receptor II sequences was accomplished using the T-Coffee program. (Notredame, et al, T-Coffee: A novel method for multiple sequence alignments. J. Molecular Biol. 302:205-217, 2000.) Synthetic peptides corresponding to these two regions were obtained and subjected to chemical and in vivo analysis as described below.

Example 2

In Vivo Activity of BBP

Methods: The osteogenic activity of material was tested using male Swiss-Weber mice aged 8 to 10 weeks were used (Taconic Farms, Germantown, N.Y.). Prior to the assay, the BBP was solubilized and lyophilized into 2 mg of atelocollagen. The dried material was placed in a #5 gelatin capsule and sterilized by exposure to chloroform vapor. To conduct the assay, mice were anesthetized using 1% isoflurane delivered in oxygen at 2 l/min through a small animal anesthesia machine (VetEquip, Pleasanton, Calif.). Animals were affixed to a surgery board and the fur over the hindquarters shaved. The skin was cleaned with 70% ethanol and a midline incision made over the spine adjacent to the hindquarters. Blunt dissection with scissors was used to expose the quadriceps muscle on one side. A small pouch was made in the muscle using the point of scissors and the #5 capsule containing the test material was inserted into the pouch. The skin was then closed with three 11 mm Michel surgical clips and the animal returned to its cage for monitoring.

After 21 days the animals were killed and the hindquarter removed. Radiological examination of the specimens was accomplished using a small parts X-Ray cabinet (Faxitron, Wheeling, Ill.). For quantization of bone formation, bone area and the bone mineral content (BMC) of an area of interest encompassing the site of ectopic bone formation was determined using a PIXImus2 small animal densitometer (GE Lunar, Madison, Wis.). Specimens were then placed in buffered formalin and submitted for routine processing for histological examination.

Various amounts of rhBMP-2 and BBP were combined and prepared for implantation. All possible combinations of the following amounts were used in pilot studies, rhBMP-2: 0 µg, 0.05 µg, 0.5 µg, 5 µg, and 50 µg; BBP: 0 µg, 50 µg, and µg 500 mg. Samples of 5 µg of rhBMP-2 were used in more extensive subsequent studies because that amount consistently produced an amount of ectopic bone that was neither too large nor too small for reliable analysis.

Results: BBP was tested alone and in combination with rhBMP-2.

FIG. 4 is a radiogram of mouse hind quarters 21 days after implantation of 500 µg of BBP in atelocollagen (top) or atelocollagen alone (bottom). When implanted alone with carrier, BBP induced calcification.

Figure 5:
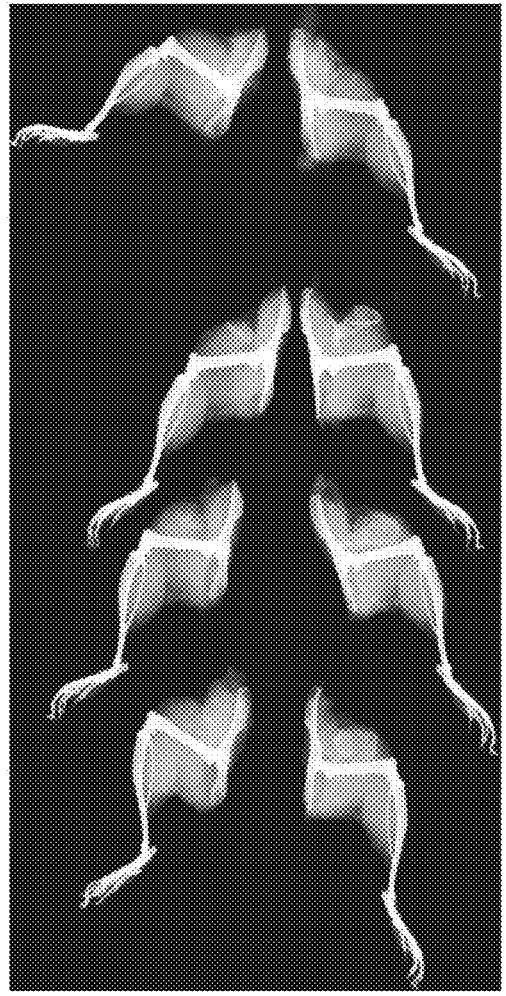
FIG. 5 is a histological section of mouse muscle 21 days after implantation of 500 µg of BBP in atelocollagen. (H & E stain. Original magnification 100×.)

FIG. 5 is a histological section of mouse muscle 21 days after implantation of 500 µg of BBP in atelocollagen. Note the dystrophic calcification primarily associated with intramuscular adipose tissue. (H & E stain. Original magnification 100×.)

When 500 µg of BBP with sequence similarity to the TGF-β receptor II was implanted with 5 µg of rhBMP-2 the amount of ectopic bone formed, as measured by densitometry, was consistently greater than the amount of bone formed in animals into which identical amounts of the rhBMP-2 alone were implanted.

Figure 6:
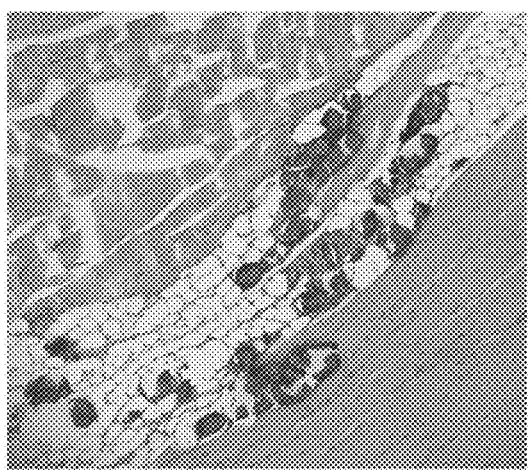
FIG. 6 are radiograms of mouse hind quarters 21 days after implantation of 5 µg of rhBMP-2 (left) or 5 µg of rhBMP-2 plus 500 mg of BBP (right).

FIG. 6 are radiograms of mouse hind quarters 21 days after implantation of 5 µg of rhBMP-2 (left) or 5 µg of rhBMP-2 plus 500 mg of BBP (right). Note the increased opacity associated with the samples containing both rhBMP-2 and BBP.

Furthermore, implants that contained both the peptide and rhBMP-2 produced detectable cartilage and bone earlier than implants of BMP-2 alone.

Figure 7:
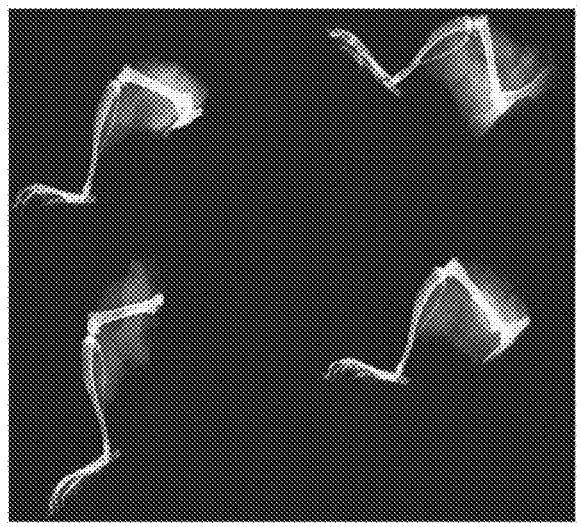
FIG. 7 are radiograms of mouse hind quarters 9 (top) and 12 (bottom) days after implantation of 5 µg of rhBMP-2 (left) or 5 µg of rhBMP-2 plus 500 mg of BBP (right).

FIG. 7 are radiograms of mouse hind quarters 9 (above) and 12 (below) days after implantation of 5 μg of rhBMP-2 (left) or 5 μg of rhBMP-2 plus 500 mg of BBP (right). Note the appearance of calcification in the sample from the day 9 sample containing both rhBMP-2 and BBP but not the sample containing BMP-2 alone.

Figure 8A:
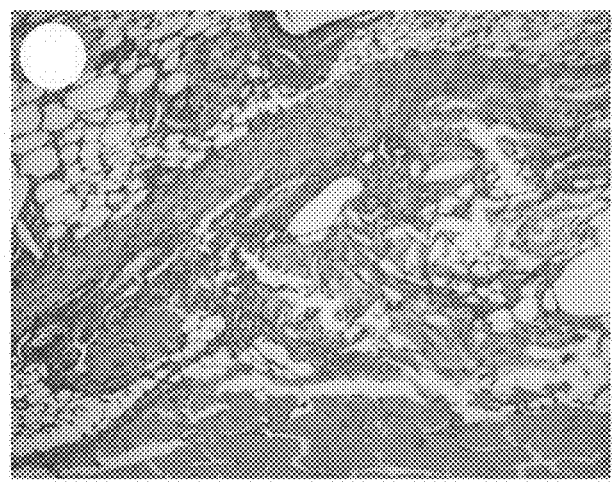
FIGS. 8A and 8B are histological sections of mouse hind quarters 9 days after implantation of 5 µg of rhBMP-2 alone (FIG. 8A) or 5 µg of rhBMP-2 plus 500 µg of BBP (FIG. 8B).
Figure 8B:

FIG. 8 are histological sections of mouse hind quarters 9 days after implantation of 5 μg of rhBMP-2 alone (A) or 5 μg of rhBMP-2 plus 500 μg of BBP (B). Note the abundant cartilage in the BMP+BBP specimen whereas the BMP alone specimen shows the earlier stages of inflammation and mesodermal cell proliferation.

TABLE 2

Densitometric quantitation of ectopic bone formation with various amounts of BBP implanted with 5 μg of rhBMP-2. Mean, SE (n).

| | BBP (μg) | | |
|---|---|---|---|
| | 0 | 50 | 500 |
| Bone Area (cm$^2$) | 0.089 ± 0.0336 (12)* | 0.159 ± 0.0606 (8) | 0.226 ± 0.0270 (12)* |
| Bone Mineral Content (g) | 0.00189 ± 0.00084 (12)** | 0.00388 ± 0.0017 (8) | 0.00528 ± 0.00068 (12)** |

*p = 0.0044;
**p = 0.0049

Example 3

Surface Plasmon Resonance to Determine the Interaction of BMP-2 and the Synthetic Peptide Methods: The binding interaction between rhBMP-2 and BBP was characterized using surface plasmon resonance employing a Biacom X instrument (Biacore, Piscataway, N.J.). Buffers and chips for the procedure were obtained from Biacore. RhBMP-2 was dialyzed into 10 mM sodium acetate, pH 5.5 at a concentration of 1 mg/ml. This material was then attached to a CM-5 sensor chip using reagents and procedures supplied by the manufacturer. Running buffer was 10 mM HEPES, pH 7.4, 150 mM NaCl, 3 mM EDTA, 0.005% Surfactant P20. The peptide was dissolved in running buffer at concentrations ranging from $1 \times 10^{-5}$ to $1 \times 10^{-4}$ M. Flow rates from 5 to 50 μl/min and injection volumes of 20 to 100 μl were employed. The regeneration solution was 10 μM glycine-HCl, pH 2.0.

Results: Results of the surface plasmon resonance studies to determine the interaction between rhBMP-2 and BBP are shown in FIG. 9.

Figure 9:
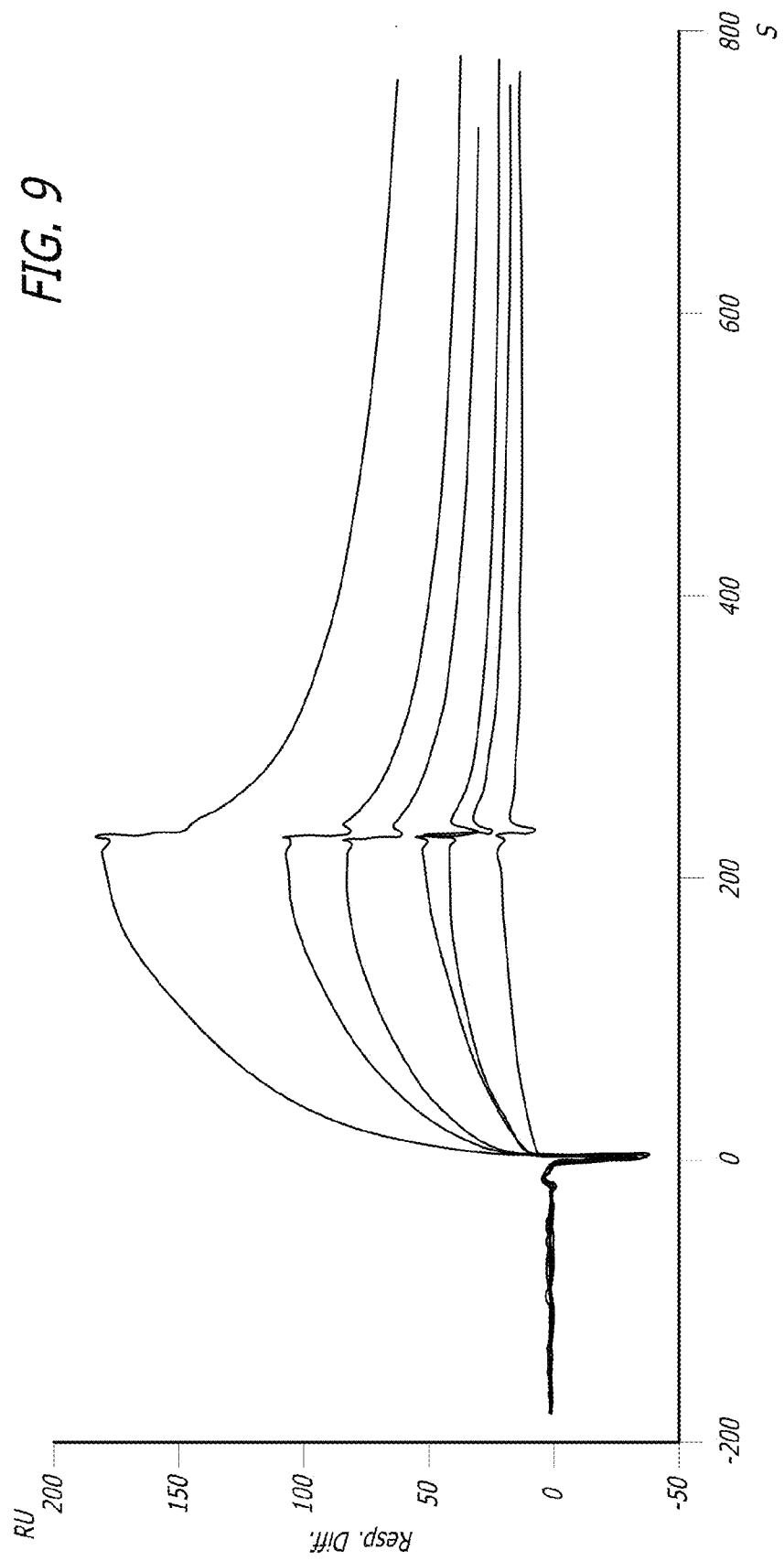
FIG. 9 is a surface plasmon resonance sensogram for the interaction of rhBMP-2 (affixed to the chip) and cyclized BBP at concentrations ranging from $1 \times 10^{-5}$ M $1 \times 10^{-4}$ M.
Figure 15:
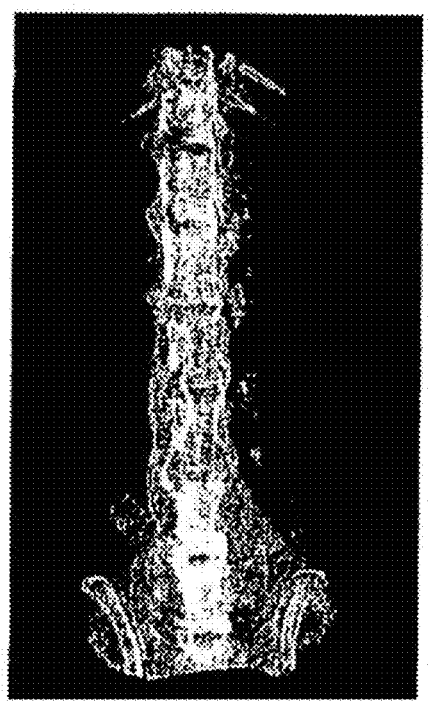
FIG. 15 is an anterior-posterior radiograph of a rat spine fused at L4-L5 with the application of BBP high dose (1000 µg)+rhBMP-2 low dose (1 µg) 8 weeks after treatment.
Figure 16:
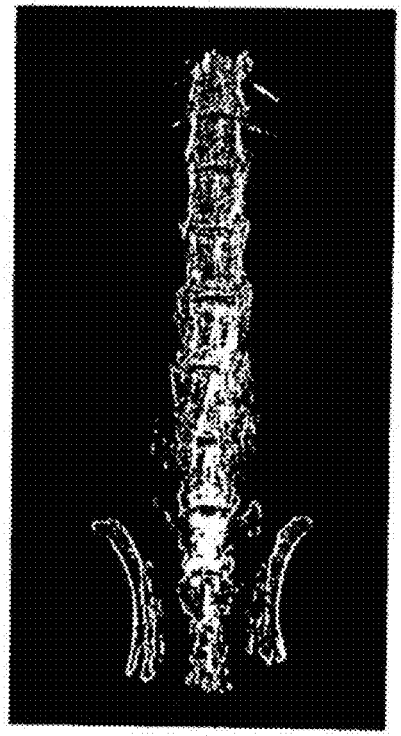
FIG. 16 is an anterior-posterior radiograph of a rat spine showing pseudoarthritis at right anno fusion at left L4-L5 with the application of rhBMP-2 (1 µg) treatment.
Figure 17:
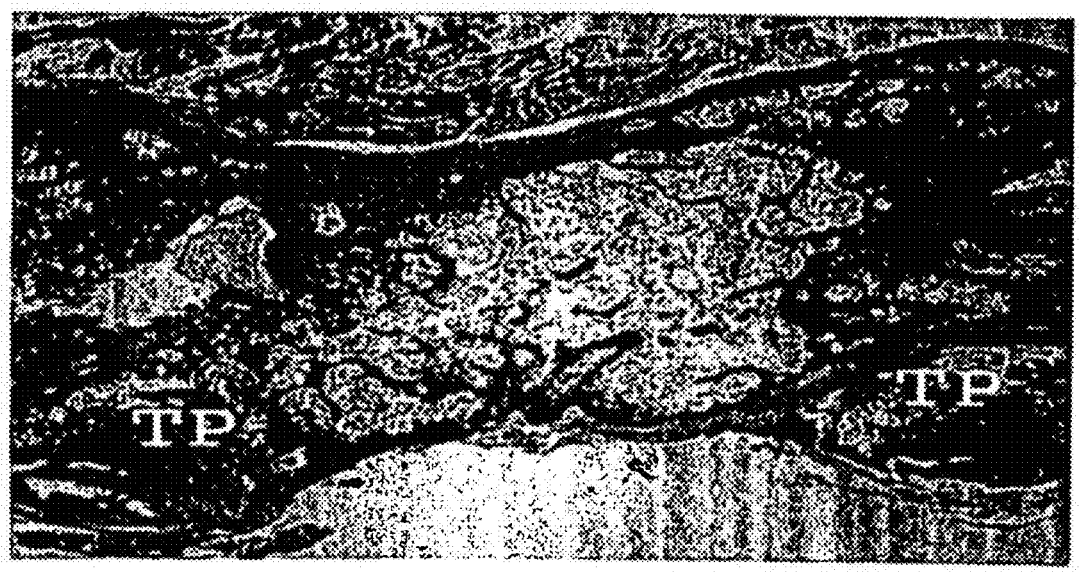
FIG. 17 is a histological section of rat spinal region 8 weeks after treatment of a combination of BBP and rhBMP-2. (H & E stain. Original magnification 8.4×.)
Figure 18:
FIG. 18 is a histological section of rat spinal region 8 weeks after treatment with low dose rhBMP-2 (1 µg). (H & E stain. Original magnification 8.4×.)

FIG. 9 is a surface plasmon resonance sensogram for the interaction of rhBMP-2 (affixed to the chip) and cyclized BBP at concentrations ranging from $1 \times 10^{-5}$ M $1 \times 10^{-4}$ M. The estimated dissociation constant ($K_D$) for the interaction was $3 \times 10^{-5}$ M. When the BBP was decyclized by prior reduction with β-mercaptoethanol, no significant binding occurred.

Example 4

Residence Time Study: BBP and rhBMP-2

Methods: Labeled rhBMP-2 was mixed with BBP or vehicle and applied to collagen sponges. The sponges were implanted into muscle pouches in rodents. At specified times (1, 3 and 7 days), the implants were removed and the amount of BMP remaining determined. Four animals were used in each group.

Results: BBP increased retention of rhBMP-2 by a factor of about two. FIG. 10 is a bar graph depicting the percentage of rhBMP-2 retention over 1, 3 and 7 days in the presence or absence of BBP.

Discussion: Increasing the retention of BMP at an implant site may improve the effectiveness of the BMP, and also reduce the amount required for the same therapeutic result.

Example 5

In Vivo Activity of Human BBP

Methods: The methods of Example 5 were utilized to test the activity of hBBP in eight mice in the hindquarter ectopic bone formation assay method using 5 μg rhBMP-2 alone (control) or 5 μg rhBMP-2 plus 0.05 mg human BBP (hBBP). After 4 weeks, the animals were killed and the hindquarter removed. X-ray and DEXA analysis were conducted.

Results: hBBP was tested in combination with rhBMP-2. When implanted, hBBP with BMP resulted in a greater amount of calcification induction than BMP alone.

TABLE 3

Densitometric quantitation of ectopic bone formation with various amounts of BBP implanted with 5 μg of rhBMP-2. Mean, SE (n).

| Group | Mean BMC content (g) |
|---|---|
| rhBMP-2 (5 μg) | 0.00775 |
| hBBP (0.05 mg) + rhBMP-2 (5 μg) | 0.01125 |

Further, BBP binding with four growth factors from the TGF-β family were assessed using surface plasmon resonance. The in vivo retention of rhBMP-2 was quantified by comparing the percentage of retained [$^{125}$I]-labeled rhBMP-2 in absorbable collagen sponge (ACS) implants with or without BBP at 1, 3, and 7 days post-implantation in rat abdominal musculature. The adjunctive effect of BBP with rhOP-1 induced bone growth was evaluated by comparing time to fusion and fusion rates in a well accepted rodent posterolateral fusion model with two different doses of rhOP-1 with and without BBP. Time to fusion was evaluated using plain radiographs. Fusion rate was determined by plain radiographs, manual palpation, and micro-computerized tomography (micro-CT). Histology was used to assess osseous characteristics of the fusion mass.

As described below, BBP bound all four TGF-β family growth factors with an intermediate affinity. The in vivo retention of BMP-2 alone ranged from about 40% on day 1 to about 30% on day 7, whereas, the retention of BMP-2 in the presence of BBP was about 85% on day 1 and about 55% on day 7. A significantly greater percentage of rhBMP-2 was retained in the presence or BBP at all time points. The addition of BBP to rhOP-1 resulted in significantly earlier and greater fusion rates than achieved with rhOP-1 alone.

It was determined that BBP enhanced osteoinductive properties of BMPs involves the binding and retention of the growth factor, resulting in a prolonged exposure of BMP to the desired fusion site. The addition of BBP to rhOP-1 resulted in significantly earlier and greater fusion rates than achieved with rhOP-1 alone. These studies support the use of BBP with BMPs to provide satisfactory fusion outcomes, while reducing the costs and side effects associated with BMP use.

Example 6

Characterization of BBP Binding with Surface Plasmon Resonance

Methods: The dynamic and equilibrium binding of BBP and the parental protein, spp24 (secreted phosphoprotein, 24 kD), with several growth factors from the TGFβ superfamily were determined using surface plasmon resonance (SPR) with a Biacore X instrument (GE Healthcare, Piscataway, N.J.). SPR is an optical technique in which the binding of an analyte (for example, BBP) to a covalently-immobilized ligand (for example rhBMP-2) on a glass chip is measured as an electrical signal proportional to the mass of analyte that binds to the chip as the running buffer containing the analyte flows over the surface. RhBMP-2, rhOP-1(rhBMP-7), rhTGF-β, and recombinant mouse GDF-5(0.4 μg each; R&D Systems, Minneapolis, Minn.) were dialyzed into 10 mM acetate buffer (pH 5.0) and amine coupled to a CM-5 sensor chip using the reagent kit supplied by the manufacturer (Biacore, GE Healthcare, Piscataway, N.J.). BBP (GenScript, Piscataway, N.J. and CS Bio, Menlo Park, Calif.) and the related protein were dissolved in HEPES-EP running buffer (10 mM HEPES, pH 7.4; 150 mM NaCl; 3 mM EDTA; and 0.005% surfactant P-20) at $1 \times 10^{-5}$ M to $1 \times 10^{-4}$ M. To ensure precise quantitation of protein concentrations, which are essential for kinetic calculations, samples were centrifuged at 12,000 rpm in a microfuge for one minute prior to use. The supernatant was decanted and used for analyses. Protein concentrations were determined using UV spectroscopy at an absorbance of 280 nm. Extinction coefficients were calculated using ProtParam tool (www.expasy.ch/tools/protparam). Flow rates ranged from 5 to 50 μl/min, and injection volumes were 20 to 100 μl. To ensure uniformity, an effort was made to react sufficient ligand to the chip to give a baseline value of about 2500 RU (response units). The kinetic constants $k_a$ (on rate, association constant, "recognition") and $k_d$ (off rate, dissociation constant, "stability") as well as the equilibrium constant $K_D$ (equilibrium constant, "affinity") were determined by a Langmuir analysis using BIAevaluation software (version 3.2) installed on the instrument by the manufacturer.

Results: The results of the kinetic analyses of the interactions between BBP or spp24 and the various growth factors are shown in Table 4.

TABLE 4

Kinetic Analysis of the Binding of BBP and spp24 to Four Growth Factors of the TGF-β Family

| Analyte | Ligand | $K_D$ ($k_d/k_a$) "affinity" M | $k_a$ "recognition" $M^{-1} s^{-1}$ | $k_d$ "stability" $s^{-1}$ |
|---|---|---|---|---|
| BBP | rhBMP-2 | $5.33 \times 10^{-8}$ | $3.17 \times 10^4$ | $1.69 \times 10^{-3}$ |
| BBP | rhOP-1 (rhBMP-7) | $1.16 \times 10^{-6}$ | $3.18 \times 10^3$ | $3.69 \times 10^{-3}$ |
| BBP | rhTGF-β | $6.8 \times 10^{-8}$ | $2.77 \times 10^4$ | $1.75 \times 10^{-3}$ |
| BBP | rmGDF-5 | $7.77 \times 10^{-7}$ | $4.53 \times 10^3$ | $3.52 \times 10^{-3}$ |
| spp24 | rhBMP-2 | $1.77 \times 10^{-8}$ | $3.11 \times 10^5$ | $5.5 \times 10^{-3}$ |

BBP = bone morphogenetic protein binding peptide
rhBMP = recombinant human bone morphogenetic protein
rhOP-1 = recombinant human osteogenic protein-1
rhTGF-β = recombinant human transforming growth factor-beta
rmGDF-5 = recombinant mouse growth and differentiation factor-5
spp24 = secreted phosphoprotein-24

BBP bound all four TGF-β family growth factors and the parental protein with an affinity that was not greatly different. RhOP-1 and GDF had the lowest affinity (highest $K_D$).

The difference in the $K_D$ for the BBP/rhOP-1 interaction and the $K_D$ for the BBP/rhBMP-2 interaction was due mostly to a lower $k_a$ (slower "recognition") in the case of the BBP/BMP-7 interaction.

The binding constants ($K_D$, "affinity") for the association of BBP with several TGF-β family growth factors and the parental protein, spp24, are slightly greater (lower affinity) than that for most receptor-ligand interactions (on the order of $K_D = 10^{-8}$ to $10^{-9}$ M) and much greater than the most avid interaction in nature ($K_D$ for streptavidin/biotin=$10^{-14}$ M). An affinity of this magnitude might be useful for providing the "slow release/immobilization" function with respect to the action of BMPs in skeletal tissue.

The $K_D$ for the BBP/rhOP-1 interaction is greater (less affinity) than that for the BBP/rhBMP-2 interaction. However, the $k_d$ (dissociation, "stability") for each of these two interactions is very similar and, therefore, may reflect a kinetic property which has increased importance in the design of therapeutics.

Example 7

Effect of BBP on BMP Retention In Vivo

Methods: The effect of BBP on the in vivo retention of rhBMP-2 was studied in 4 to 6 week old female Sprague-Dawley rats. Briefly, 5 mg of cold rhBMP-2 and about $1 \times 10^5$ cpm of [$^{125}$I]-labeled rhBMP-2 in 50 ml were applied to absorbable cross-linked collagen sponges (ACS; 14×14×3 mm; Helistat, Integra Life Sciences, Plainsboro, N.J.) in the presence of vehicle or 0.5 mg BBP. After approximately 10 minutes of incubation at room temperature the preparation was implanted by inserting it into a blind pouch created by gentle blunt dissection in the abdominal musculature. There were four samples for each treatment/time point (2 samples per rat and 2 rats per time point). The tracer retention was measured at 1, 3, and 7 days post-implantation by recovering the implants employing using a gamma-counter. Aliquots of the application fluids were counted at the time of implantation to determine total cpm at $t_o$. The percent of applied rhBMP-2 retained was calculated at each time point by dividing the explant-associated cpm with the cpm implanted at $t_o$.

Results: The effect of BBP on BMP-2 retention in vivo is shown in Table 5.

TABLE 5

Effect of BBP on the Retention of BMP-2 in vivo (Percent BMP-2 Retained)

| Treatment | Day 1 | Day 3 | Day 7 |
|---|---|---|---|
| BMP-2 alone | 40.9 ± 1.51 | 31.9 ± 2.07 | 27.9 ± 2.48 |
| BMP-2 + BBP | 83.3 ± 1.56* | 70.6 ± 1.34* | 53.0 ± 1.51* |

Data is shown as the mean ± S.E. n = 4 for all groups.
*Significantly greater percentage of rhBMP-2 retained compared to group without BBP (p ≤ 0.0001)

Retention of BMP-2 alone ranged from about 40% on day 1 to about 30% on day 7. On the other hand, the retention of BMP-2 implanted in the presence of BBP was about 85% on day 1 and about 55% on day 7. A significantly greater percentage of rhBMP-2 was retained in the presence or BBP at all time points (p≤0.0001).

The results of the BMP retention study support the hypothesis that BBP enhances BMP activity by increasing the retention of BMP at the implant site. The theory that, if a higher concentration of BMP is present for a longer period of time, a greater biological effect would be expected. BMPs induce a recapitulation of endochondral bone formation, which is to say that the tissue at the implant site goes through a defined and reproducible progression including inflammation, mesodermal stem cell proliferation, cartilage formation, and vascular invasion with replacement of cartilage by bone. This process requires a period of many days and each of the early steps is dependant on BMP. Thus, a delay in the dispersal of BMP will result in a greater concentration of the morphogen many days after implantation and, therefore, an enhancement of processes such as chrondrogenic differentiation of mesodermal stem cells. From these results, one would expect a similar clinical response to a smaller dose of BMP when used in conjunction with BBP.

Example 8

In Vivo Posterolateral Fusion Study Design

Methods: A total of 120 male Lewis rats (8 weeks of age, 200-260 g, Charles River, Wilmington, Mass.) were divided into 8 groups. Groups differed only by the materials added to the ACS (5×5×13 mm) that were applied to the surgical sites. The preparation of the implants was previously described in detail. (Alanay, et al., The adjunctive effect of a binding peptide on bone morphogenetic protein enhanced bone healing in a rodent model of spinal fusion. *Spine* 2008; 33:1709-13). Implanted rhOP-1 was obtained from Stryker Biotech, Hopkinton, Mass. The control groups were: (I) Decortication alone (n=10); (II) ACS only (n=10); (III) ACS with 1000 μg BBP (n=10); and (IV) ACS with 10 μg rhOP-1 (n=10). The experimental groups were: (V) ACS with 3 μg rhOP-1 (n=20); (VI) ACS with 3 μg rhOP-1 plus 1000 μg BBP (n=20); (VII) ACS with 1 μg rhOP-1 (n=20); (VIII) ACS with 1 μg rhOP-1 plus 1000 μg BBP (n=20) (see Table 6). Animals were sacrificed 8 weeks after surgery with $CO_2$.

Surgical Technique. Animals were anesthetized with 2-2.5% isoflurane administered in oxygen (1 L/min) and the surgical site was shaved and disinfected with alternative betadine and 70% alcohol. Animals were premedicated with 0.15 mg buprenorphine and postoperatively received tapered doses every 12 hours for 2 days.

The posterolateral intertransverse process spinal fusion at L4-L5 in the rat is a well established model in our laboratory. The iliac crest was used as a landmark to locate the body of the L6 vertebra. A 4-cm longitudinal midline incision was made through the skin and subcutaneous tissue over L4-L5 down to the lumbodorsal fascia. Then a 2 cm longitudinal paramedical incision was made in the paraspinal muscles bilaterally. The transverse processes of L4-L5 were exposed, cleaned of soft tissue, and decorticated with a high-speed burr. The surgical site was then irrigated with sterile saline and identical treatment materials were placed bilaterally, taking care to apply the implant to fully cover the transverse processes. The paraspinal muscles were then allowed to cover the implants and the lumbodorsal fascia and skin were closed with 4-0 Prolene sutures (Ethicon Inc., Somerville, N.J.). Animals were allowed to ambulate, eat, and drink ad libitum immediately after surgery.

Radiographic Analysis. Posteroanterior radiographs were taken on each animal at 4, 6, and 8 weeks using an AMX-3 portable X-ray instrument (GE Healthcare, Piscataway, N.J.). Radiographs were evaluated by 3 independent observers employing the following standardized scale: 0: no fusion; 1: incomplete fusion with bone formation present; and 2: complete fusion. The scores from the observers were added together and a score of 5 or 6 was considered "fused."

Manual Assessment of Fusion. Eight weeks after surgery, the spines were removed and evaluated by three blinded independent observers for intersegmental motion. Any motion on either side between the facets or transverse processes, including unilateral movement, was considered nonunion. The bilateral absence of movement was considered fusion. Spines were scored as either fused or not fused. Unanimous agreement was required to consider a spine to be "fused".

Microcomputerized Tomography Analysis. The explanted spines were subsequently scanned using high-resolution microcomputerized tomography (micro-CT), using 9-20 μm resolution technology (μCT40, SCANCO Medical, Basserdorf, Switzerland) to further assess the fusion rate and observe the fusion mass. Fusion was defined as the bilateral presence of bridging bone between the L4 and L5 transverse processes. Micro-CT data were collected at 55 kVp and 72 μA and reconstructed using a cone-beam algorithm supplied with the micro-CT scanner. Visualization and data reconstruction were performed using μCT Ray T3.8 and μCT Evaluation Program V6.0 (SCANCO Medical), respectively. The reconstructed images were judged to be fused or not fused by an experienced independent observer.

Histological Analysis. The spines were dissected and fixed in 10% formalin, then transferred to 70% denatured ethanol. When imaging was completed, the specimens were decalcified using a commercial reagent containing 10% HCl (Cal-Ex, Fisher Scientific, Fairlawn, N.J.), washed with running tap water, and then transferred to 70% denatured ethanol. Serial sagittal sections were carefully cut at the level of the transverse process. The specimens were then embedded in paraffin, sectioned, and stained with hematoxylin and eosin. Each sample which displayed any fusion was processed for histological examination to ensure that the fusion mass represented true bone formation and not dystrophic calcification or some other clinically disadvantageous process. Samples with no fusion mass were not examined.

Statistical Analysis. All statistical analyses were performed with Statistical Package for the Social Sciences (SPSS, V17, Chicago, Ill.). RhBMP-2 retention was compared using Student's t-test. Fusion rates were compared in sequential two-group comparisons using Fisher's exact test. Inter-observer reliability was assessed by computing the κ-statistic. Agreement was graded as follows: poor, κ=0-0.2; fair, κ=0.21-0.4; moderate, κ=0.41-0.60; substantial, κ=0.61-0.8; and excellent, κ>0.81. A value of 1 indicates absolute agreement, whereas a value of 0 indicates agreement no better than chance.

Results: Surgical Outcomes. No abnormal behavior was noted in the 120 operated rats. None of the rats died before the end of the study. There were no surgical complications and no rats showed any neurological deficits during the 8-week follow-up period.

Figure 19A:
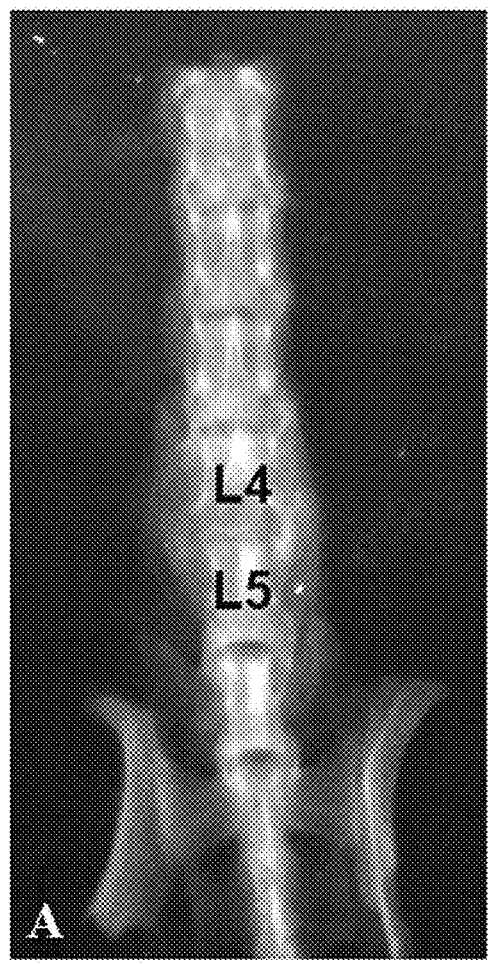
FIGS. 19A and 19B are posteroanterior radiographs of explanted rat spines obtained after eight weeks of treatment with (FIG. 19A) 3 µg rhOP-1+BBP and (FIG. 19B) 3 µg rhOP-1.
Figure 19B:
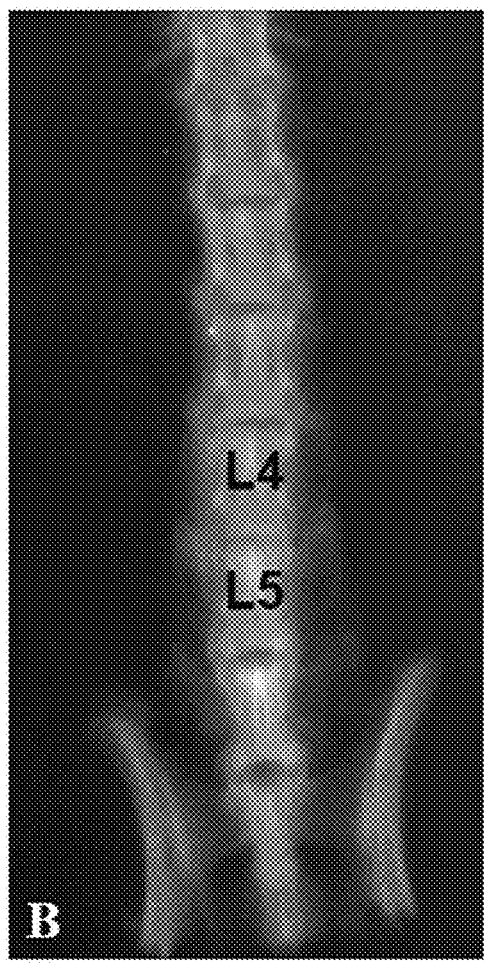

Radiographic Analysis. Radiographs of the rat spines were obtained at 4, 6, and 8 weeks (FIG. 19). Table 6 shows the proportion of rats in each group that had a total fusion score of 5 or 6 and was, therefore, judged to be fused at the specified time point.

TABLE 6

Radiological evaluation of treatments. Percents of subjects showing satisfactory radiological spine fusion.

| Group | Treatment | 4 wk (%) | 6 wk (%) | 8 wk (%) |
|---|---|---|---|---|
| I | Decortication only | 0 | 0 | 0 |
| II | ACS alone | 0 | 0 | 0 |
| III | ACS + 1000 µg BBP | 0 | 0 | 0 |
| IV | ACS + 10 µg rhOP-1 | 50 | 80 | 100 |
| V | ACS + 3 µg rhOP-1 | 30 | 45 | 55 |
| VI | ACS + 3 µg rhOP-1 + 1000 µg BBP | 40 | 80* | 90* |
| VII | ACS + 1 µg rhOP-1 | 0 | 10 | 20 |
| VIII | ACS + 1 µg rhOP-1 + 1000 µg BBP | 0 | 30 | 60* |

*Significantly greater fusion rate when compared to group without BBP ($p < 0.05$)
ACS = absorbable collagen sponge
BBP = bone morphogenetic protein binding peptide
rhOP-1 = recombinant human osteogenic protein-1

TABLE 7

Fusion Rate Based on Manual Palpation and Micro-CT at 8 Weeks

| Treatment | Manu (%) | Micro (%) |
|---|---|---|
| Decortication only | 0 | 0 |
| ACS alone | 0 | 0 |
| ACS + 1000 µg BBP | 0 | 0 |
| ACS + 10 µg rhOP-1 | 100 | 100 |
| ACS + 3 µg rhOP-1 | 55 | 55 |
| ACS + 3 µg rhOP-1 + 1000 µg BBP | 90* | 90* |
| ACS + 1 µg rhOP-1 | 10 | 10 |
| ACS + 1 µg rhOP-1 + 1000 µg BBP | 50* | 50* |

*Significantly greater fusion rate when compared to group without BBP ($p < 0.05$)
† Statistically indistinguishable from high-dose rhOP-1 control group ($p = 0.54$)
ACS = absorbable collagen sponge
BBP = bone morphogenetic protein binding peptide
rhOP-1 = recombinant human osteogenic protein-1

The inter-observer agreement was substantial to excellent at all time points ($\kappa=0.763$ to $0.895$). None of the animals in the decortication only, ACS only, or ACS with BBP groups showed any sign of bone formation during the 8-week follow-up period. Group VI (3 µg rhOP-1+BBP) had a higher fusion rate than Group V (3 µg rhOP-1) at all time points. This difference in fusion rate was significant at 6 and 8 weeks ($p=0.048$ and $0.031$, respectively). Group VIII (1 µg rhOP-1+BBP) had a higher fusion rate than Group VII (1 µg rhOP-1) at 6 and 8 weeks; however, this difference was only significant at 8 weeks ($p=0.022$). There was no statistically significant difference between the fusion rates of Groups IV (10 µg rhOP-1) and VI (3 µg rhOP-1+BBP).

Manual Palpation. The proportions of rats in each group that were judged to be fused by three independent evaluators are shown in Table 4. The inter-observer agreement was excellent among these observers ($\kappa=0.966$ to $0.983$). The critical comparisons were between rhOP-1 with and without the addition of BBP. Eleven spines in Group V (3 µg rhOP-1) were assessed as fused (55% fusion rate), whereas 18 spines in Group VI (3 µg rhOP-1+BBP) were considered fused (90% fusion rate). This observed difference was a statistically significant ($p=0.031$). A similar treatment effect was seen when comparing Group VII (1 µg rhOP-1) with a 10% (2/20) fusion rate to Group VIII (1 µg rhOP-1+BBP) with a 50% (10/20) fusion rate. This observed difference was also statistically significant ($p=0.014$). There was no significant difference between the fusion rates of Groups IV (10 µg rhOP-1) and VI (3 µg rhOP-1+BBP).

Micro-CT Analysis. Table 7 shows the proportions of subjects in each group judged to be fused. The observed fusion rates were consistent with those determined with the use of manual palpation and radiographic analyses. The spines of the rats in groups VI and VIII exhibited considerable bone formation when compared to their respective control groups without BBP (V and VII). The new bone masses were solidly fused and no gaps were detected between the transverse processes. Multiple cut sections were reconstructed to evaluate the presence of a bony bridge between the transverse processes. Trabeculae bridging the transverse processes were consistently observed in the cut-plane images of all spine samples deemed to be fused. The bridging trabecular bone was thicker in the groups with BBP when compared to their respective control groups without BBP. Groups I, II, and III which included no OP-1 did not exhibit any bony bridging between the transverse processes. A cleft was observed between the L4 and L5 transverse processes in all spines judged to be not fused (FIG. 20).

Histological Analysis. A representative histological section from a specimen with a successful fusion is shown in FIG. 21. Mature trabecular bone in the fusion mass and extensive remodeling of the mass and the transverse process can be seen. The thickness and maturity of the fusion mass tended to be greater in the groups with BBP as compared to those with the same dose of rhOP-1 alone.

In the posterolateral intertransverse process fusion portion of this study, the radiographic results demonstrated significantly higher rates of fusion and earlier fusion when rhOP-1 was used in conjunction with BBP than when rhOP-1 was used alone. These findings were further confirmed after harvesting the spines and subjecting them to manual palpation and micro-CT analysis. Although manual palpation is the current gold standard in the evaluation of spinal fusion in this model, the results of manual palpation and micro-CT were identical and correlated well with radiographic outcomes at the end of the study. BBP by itself did not induce any degree of fusion. Nor was ectopic calcification observed in the BBP only treatment groups. These results are consistent with prior reports which found that BBP alone did not induce ectopic bone formation but who did observe small amounts of dystrophic calcification in association with intramuscular adipose and other reports which also did not find any spinal fusion in animals treated with BBP alone. Additionally, the combination of 3 µg rhOP-1 with 1000 µg BBP achieved a fusion rate statistically indistinguishable to that achieved by high dose (10 µg) rhOP-1 alone. This illustrates the potential for BBP combined with a lower dose of rhOP-1 to achieve similar outcomes as a high dose of rhOP-1 alone.

By way of example only, BBP may be made adherent to the implant in a number of ways, including spraying BBP onto a prepared metallic or plastic surface. BBP may also be attached in a slurry of another material, such as collagen or ceramic. Additionally, BBP and a growth factor (such as a TGF-β family member, BMP-2, OP-1/BMP-7, GDF-5 and TGF-β, for example) may be applied to a collagen sponge and implanted at a surgical site where bone growth is desired, including orthopedic situations (such as spinal fusion, reconstructive surgery and fracture healing), dental applications (such as dental implants), and in metabolic bone disorders (such as osteoporosis, where implants may be used in vulnerable skeletal sites).

While the specification describes particular embodiments of the present invention, those of ordinary skill can devise variations of the present invention without departing from the inventive concept.

What is claimed is:

1. A method of enhancing the rate or degree of bone formation in a vertebrate, comprising applying to a desired site a combination of bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member growth factor, wherein the BBP maintains an amount of growth factor at a site longer than the presence of the amount of growth factor alone.

2. A method of enhancing the rate or degree of bone formation in a vertebrate, comprising applying to a desired site a combination of bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member growth factor, wherein the BBP has a dissociation constant with the growth factor sufficient to retain an amount of growth factor at a site longer than the presence of the amount of growth factor alone.

3. A method of enhancing the rate or degree of bone formation in a vertebrate, comprising applying to a desired site a combination of bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member growth factor, wherein the BBP has an equilibrium constant with the growth factor sufficient to retain an amount of growth factor at a site longer than the presence of the amount of growth factor alone.

4. The method of claim 2, wherein the dissociation constant is about $1.0 \times 10^{-3}$ to about $6.0 \times 10^{-3}$.

5. The method of claim 2, wherein the equilibrium constant is about $5.0 \times 10^{-8}$ to about $1.0 \times 10-6$.

6. A method of enhancing the rate or degree of bone formation in a vertebrate, comprising applying to a desired site a combination of bone morphogenic (BMP) Binding Peptide BBP) having the amino acid sequence of SEQ ID NO:11, SEQ ID NO:1, or SEQ ID NO:13, and at least one transforming growth factor-beta (TGF-β), family member, wherein the BBP retains an amount of the TGF-β family member at the desired site longer than the amount of the TGF-β family member alone.

7. A method of enhancing the rate or degree of bone formation in a vertebrate, comprising applying to a desired site a combination of bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member, wherein the BBP retains TGF-β family member at a higher concentration at the desired site longer than the presence of the TGF-β family member alone.

8. A method of enhancing the rate or degree of bone formation in a vertebrate, comprising applying to a desired site a combination of bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member, wherein the BBP increases the duration of exposure of an amount of the TGF-β family member at the site relative to the amount of the TGF-β family member alone.

9. The method of any one of claims 1-8, wherein the TGF-β family member is selected from the group comprising: BMP-2, BMP-4, BMP-7, TGF-β or GDF-5.

10. A method of enhancing the rate or degree of mesodermal stem cell proliferation in bone, comprising applying to a desired site bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member, wherein the BBP retains the TGF-β family at the tissue longer than the presence of the TGF-β family member alone.

11. A method of enhancing the rate or degree of chondrogenesis in bone, comprising applying to a desired site bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member, wherein the BBP retains the TGF-β family at the tissue longer than the presence of the TGF-β family member alone.

12. A method of enhancing the rate or degree of osteogenesis in bone, comprising applying to a desired site bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member, wherein the BBP retains the TGF-β family at the tissue longer than the presence of the TGF-β family member alone.

13. A method of enhancing the rate or degree of calcification in bone, comprising applying to a desired site bone morphogenic (BMP) Binding Peptide (BBP) having the amino acid sequence of SEQ ID NO:11, SEQ ID NO:1, or SEQ ID NO:13, and at least one transforming growth factor-beta (TGF-β) family member, wherein the BBP retains the TGF-β family at the tissue longer than the presence of the TGF-β family member alone.

14. The method of any one of claims 10-13, wherein the TGF-β family member is selected from the group comprising: BMP-2, BMP-4, BMP-7, TGF-β or GDF-5.

* * * * *